US011964147B2

(12) United States Patent
Bauer et al.

(10) Patent No.: US 11,964,147 B2
(45) Date of Patent: Apr. 23, 2024

(54) CRANIAL IMPLANT FOR DEVICE FIXATION IN BURR HOLES

(71) Applicant: Medtronic, Inc., Minneapolis, MN (US)

(72) Inventors: Ryan T. Bauer, Plymouth, MN (US); Byron Johnson, Coon Rapids, MN (US); Arnis L. Kurmis, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 361 days.

(21) Appl. No.: 16/376,543

(22) Filed: Apr. 5, 2019

(65) Prior Publication Data
US 2019/0308025 A1 Oct. 10, 2019

Related U.S. Application Data

(60) Provisional application No. 62/653,905, filed on Apr. 6, 2018.

(51) Int. Cl.
*A61N 1/05* (2006.01)
*A61B 17/34* (2006.01)
*A61N 1/375* (2006.01)

(52) U.S. Cl.
CPC ........ *A61N 1/0539* (2013.01); *A61B 17/3468* (2013.01); *A61N 1/0534* (2013.01); *A61N 1/37514* (2017.08)

(58) Field of Classification Search
CPC .............. A61N 1/37514; A61N 1/0534; A61N 1/0558; A61N 1/0539; A61N 1/057;
(Continued)

(56) References Cited

U.S. PATENT DOCUMENTS 4,998,938 A * 3/1991 Ghajar .................. A61B 90/11
285/206
6,356,792 B1 * 3/2002 Errico .................. A61N 1/0534
606/129
(Continued)

FOREIGN PATENT DOCUMENTS

| EP | 2070561 A1 | 6/2009 |
| EP | 2653188 A1 | 10/2013 |
| WO | 2006/105463 A2 | 10/2006 |

OTHER PUBLICATIONS

Saddle Definition, accessed Jan. 15, 2022 from https://www.lexico.com/en/definition/saddle from Lexico.com (Year: 2022).*
(Continued)

*Primary Examiner* — Kankindi Rwego
(74) *Attorney, Agent, or Firm* — Shumaker & Sieffert, P.A.

(57) ABSTRACT

A cranial implant may include an interior guide portion, an exterior guide portion, and one or more flanges. In one example, the interior guide portion may be disposed in a burr hole of a cranium and include a distal end, a proximal end, an inner surface, and an outer surface. The distal end may be inserted further into the burr hole than the proximal end. The inner surface may at least partially define a channel that accepts an elongated member, and the outer surface may extend around the full circumference of the burr hole. The exterior guide portion may be coupled to the interior guide portion and may contact an external surface of the cranium. The interior guide portion may define one or more surface features configured to secure the interior guide portion to the burr hole or secure an elongated member within the channel of the cranial implant.

21 Claims, 20 Drawing Sheets

(58) Field of Classification Search
CPC ............... A61N 1/059; A61B 17/3468; A61B 2017/3484; A61B 17/3423; A61B 17/3472; A61B 2017/3492
USPC .......................................................... 606/129
See application file for complete search history.

(56) References Cited

U.S. PATENT DOCUMENTS

| | | | | |
|---|---|---|---|---|
| 8,380,323 | B2* | 2/2013 | Rossby | A61B 90/10 607/116 |
| 9,020,606 | B2* | 4/2015 | Yin | A61N 1/0539 607/116 |
| 2005/0015128 | A1* | 1/2005 | Rezai | A61N 1/0539 607/115 |
| 2005/0143800 | A1* | 6/2005 | Lando | A61N 1/0539 607/116 |
| 2005/0182420 | A1* | 8/2005 | Schulte | A61N 1/0539 606/130 |
| 2006/0115520 | A1 | 6/2006 | Vanek et al. | |
| 2006/0129203 | A1* | 6/2006 | Garabedian | A61N 1/0531 607/45 |
| 2009/0112278 | A1* | 4/2009 | Wingeier | A61B 5/4064 607/45 |
| 2009/0157157 | A1* | 6/2009 | Schorn | A61M 25/02 607/149 |
| 2012/0245529 | A1 | 9/2012 | Hummen et al. | |
| 2013/0066410 | A1 | 3/2013 | Funderburk | |
| 2015/0141926 | A1* | 5/2015 | Asaad | A61N 1/0539 604/175 |

OTHER PUBLICATIONS

Flange definition, accessed Jan. 15, 2022 from https://www.merriam-webster.com/dictionary/flange from Merriam-Webster, Incorporated (Year: 2022).*
International Preliminary Report on Patentability from International Application No. PCT/US2019/026032, dated Oct. 15, 2020, 9pp.
International Search Report and Written Opinion of International Application No. PCT/US2019/026032, dated Jul. 4, 2019, 15 pp.
Response to Communication under Rule 161/162 dated Nov. 19, 2020, from counterpart European Patent Application No. 19718990.5, filed May 26, 2021, 20 pp.

* cited by examiner

CRANIAL IMPLANT FOR DEVICE FIXATION IN BURR HOLES

This application claims the benefit of U.S. Provisional Patent Application No. 62/653,905, filed on Apr. 6, 2018, the entire contents of which is incorporated by reference herein.

FIELD

The disclosure relates to medical devices, e.g., a medical device configured to be inserted into the cranium of a patient and fix another device to the cranium.

BACKGROUND

Medical devices may be external or implanted. Depending on the application for which they are implanted in a patient, medical devices may include a variety of electrical and/or mechanical components. Certain medical devices may be fixed or secured to a portion of the anatomy. For example, electrical leads or catheters used to deliver a therapy to a patient may be secured to a cranium of a patient.

SUMMARY

This disclosure is directed to medical devices configured to fix or secure elongated members to a cranium of a patient. An elongated member, such as an electrical lead or a drug delivery catheter, may be coupled to a medical device (e.g., an electrical stimulator or drug pump) and inserted through a burr hole to reach a target location of the brain. The cranial implants described herein may include an interior portion (e.g., a fully cylindrical portion or an arcuate guide portion) that is placed within the burr hole to stabilize the elongated member within the burr hole. The fully cylindrical portion may provide a complete circumferential cross-section, and the arcuate guide portion may extend partially around the circumference of the burr hole. The cranial implant may also have an exterior guide portion coupled to the interior portion, wherein the exterior guide portion defines a channel that accepts and secures a portion of the elongated member disposed external from the burr hole.

In some examples, the interior portion (e.g., the fully cylindrical portion or the arcuate guide portion) positioned within the burr hole may provide sufficient stability that no additional structures are needed to secure the elongated member. In other examples, one or more bone screws may attach a portion of the exterior guide portion to the cranium, or a fixation plate or fixation cap may be attached to the cranium and secure the elongated member within the cranial implant. A fixation cap may be configured to at least partially cover the cranial implant and, when attached to the cranium, prevent the elongated member from moving relative to the burr hole In one example, the disclosure describes a cranial implant that includes an arcuate guide portion configured to be disposed in a burr hole of a cranium, the arcuate guide portion comprising a distal end, a proximal end, an inner surface, and an outer surface, the distal end configured to be inserted further into the burr hole than the proximal end, and the inner surface configured to at least partially define a first channel that accepts an elongated member, wherein the outer surface extends around less than a full circumference of the burr hole, an exterior guide portion coupled to the arcuate guide portion and configured to contact an external surface of the cranium, the exterior guide portion defining a second channel configured to accept the elongated member, and one or more flanges coupled to the exterior guide portion and configured to retain the elongated member at least partially within the second channel.

In another example, a cranial implant system includes a cranial implant having an arcuate guide portion configured to be disposed in a burr hole of a cranium, the arcuate guide portion comprising a distal end, a proximal end, an inner surface, and an outer surface, the distal end configured to be inserted further into the burr hole than the proximal end, and the inner surface configured to at least partially define a first channel that accepts an elongated member, wherein the outer surface extends around less than a full circumference of the burr hole, an exterior guide portion coupled to the arcuate guide portion and configured to contact an external surface of the cranium, the exterior guide portion defining a second channel configured to accept the elongated member; and one or more flanges coupled to the exterior guide portion and configured to retain the elongated member at least partially within the second channel, and a fixation cap configured to at least partially cover the cranial implant and define a routing channel for at least a portion of the elongated member.

In another example, a method includes inserting an elongated member from an exterior of a cranium through a burr hole and to a target site within the cranium, and inserting a cranial implant configured to retain the elongated member with respect to the cranium, the cranial implant including an arcuate guide portion configured to be disposed in the burr hole of the cranium, the arcuate guide portion comprising a distal end, a proximal end, an inner surface, and an outer surface, the distal end configured to be inserted further into the burr hole than the proximal end, and the inner surface configured to at least partially define a first channel that accepts the elongated member, wherein the outer surface extends around less than a full circumference of the burr hole, an exterior guide portion coupled to the arcuate guide portion and configured to contact an external surface of the cranium, the exterior guide portion defining a second channel configured to accept the elongated member, and one or more flanges coupled to the exterior guide portion and configured to retain the elongated member at least partially within the second channel.

In another example, a cranial implant includes an interior guide portion configured to be disposed in a burr hole of a cranium, the interior guide portion comprising a first distal end, a first proximal end, a first inner surface, and a first outer surface, the distal end configured to be inserted further into the burr hole than the proximal end, and the first inner surface at least partially defines a channel configured to accept an elongated member and one or more structures defined to retain the elongated member at least partially within the channel; and an exterior guide portion extending from the interior guide portion and configured to contact an external surface of the cranium, the exterior guide portion comprising a second distal end, a second proximal end, a second inner surface, and a second outer surface, wherein the second inner surface at least partially defines the channel extending from the interior guide portion, and wherein a second diameter of the outer surface of the exterior guide portion is larger than a first diameter of the first outer surface of the interior guide portion.

In another example, a system includes a cranial implant that includes an interior guide portion configured to be disposed in a burr hole of a cranium, the interior guide portion comprising a first distal end, a first proximal end, a first inner surface, and a first outer surface, the distal end configured to be inserted further into the burr hole than the proximal end, and the first inner surface at least partially defines a channel configured to accept an elongated member; and an exterior guide portion extending from the interior guide portion and configured to contact an external surface of the cranium, the exterior guide portion comprising a second distal end, a second proximal end, a second inner surface, and a second outer surface, wherein the second inner surface at least partially defines the channel extending from the interior guide portion, and wherein a second diameter of the outer surface of the exterior guide portion is larger than a first diameter of the first outer surface of the interior guide portion; and a plug retainer configured to contact the exterior guide portion.

In another example, a method includes inserting a cranial implant into a burr hole configured to retain an elongated member with respect to the cranium, the cranial implant includes an interior guide portion configured to be disposed in a burr hole of a cranium, the interior guide portion comprising a distal end, a proximal end, an inner surface, and an outer surface, the distal end configured to be inserted further into the burr hole than the proximal end, and the inner surface configured to at least partially define a channel that accepts an elongated member; and an exterior guide portion extending from the interior guide portion and configured to contact an external surface of the cranium, the exterior guide portion comprising a distal end, a proximal end, an inner surface, and an outer surface, and the inner surface configured to at least partially define the channel extending from the interior guide portion, wherein a diameter of the outer surface of the exterior guide portion is larger than a diameter of the outer surface of the interior guide portion; and inserting the elongated member from an exterior of a cranium through a burr hole and to a target site within the cranium The details of one or more examples are set forth in the accompanying drawings and the description below. Other features, objects, and advantages of the disclosure will be apparent from the description and drawings, and from the claims.

DETAILED DESCRIPTION

Figure 1:
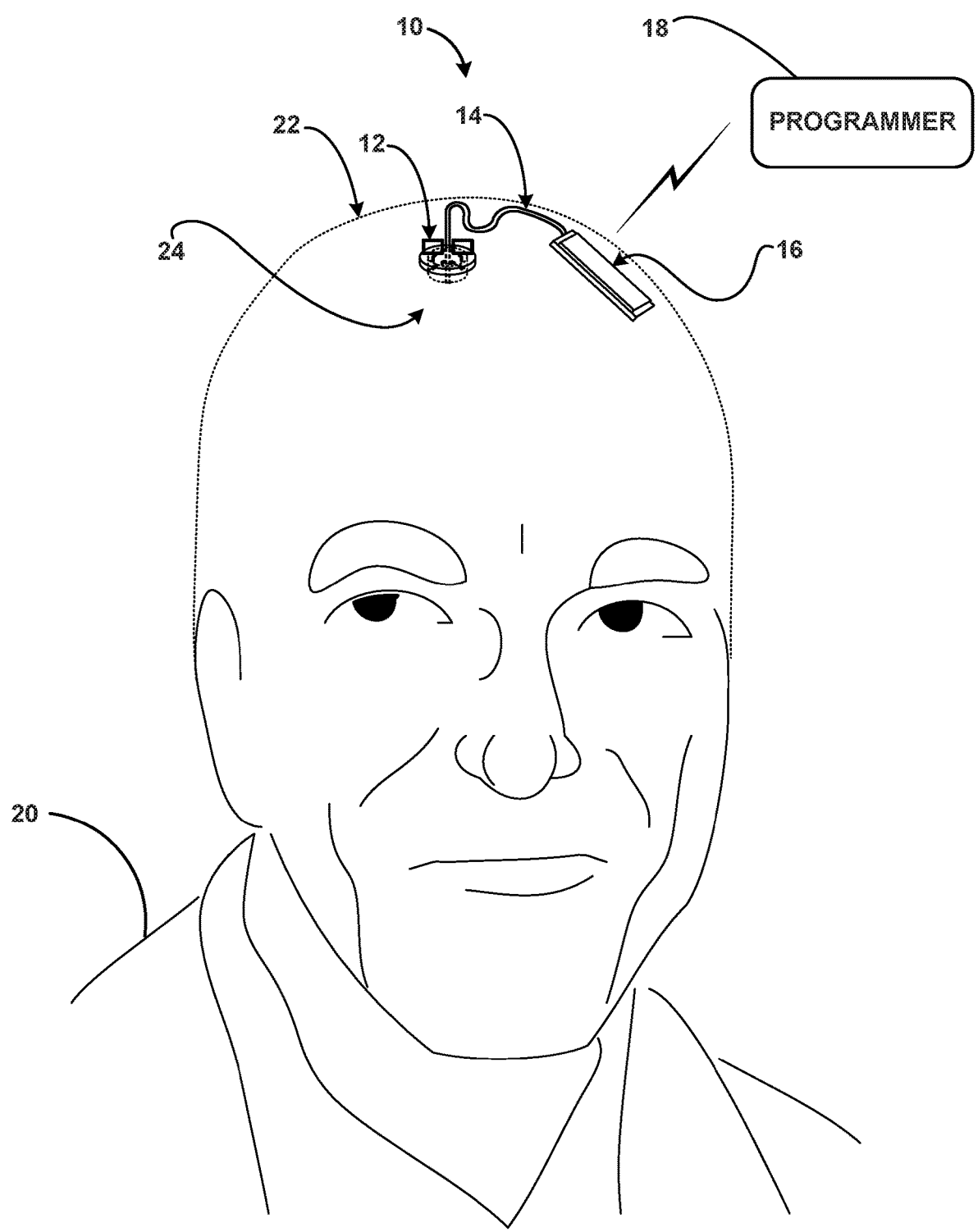
FIG. 1 is a conceptual diagram illustrating an example cranial implant system, in accordance with one or more aspects of this disclosure.

In general, this disclosure is directed to medical devices configured to secure elongated members, such as medical leads or catheters, to a cranium of a patient. In order to treat certain diseases or disorders, an elongated member such as an electrical stimulation lead or a drug delivery catheter, for example, may be implanted within the cranium of a patient. Typically, the elongated member is coupled to a medical device outside of the cranium, passes through a burr hole created in the cranium, and then the distal end of the elongated member is disposed at a target location within the brain. The burr hole is usually a circular hole created in the cranium and sized much larger than the elongated member to allow the physician to place the elongated member at a variety of locations within the burr hole to reach a desired entry point in outer portion of the brain to reach the target site in the brain. In addition, the larger burr hole may allow the clinician to identify and avoid arteries or veins when inserting the elongated member into the brain or otherwise make changes to originally planned implant locations without removing additional portions of cranial bone.

In some cases, a burr hole cap may be inserted inside of the burr hole to maintain the physician selected position within the burr hole. However, these burr hole caps are typically designed to be disposed within large burr holes (e.g., 13 or 14 mm diameter) and are too large to work with smaller burr holes that do not allow for different lead locations within the burr hole. In smaller burr holes just large enough to accept the elongate member, a clinician may screw a flat metal plate on the cranium to sandwich the elongated member between the cranium and the flat plate. However, this securing technique may not sufficiently anchor the elongate member within the burr hole and may damage the elongate member. In addition, the metal plate may be a source of heat from induced eddy currents during recharging of a medical device on the cranium and attached to the elongated member.

As described herein, systems, devices, and techniques are described that facilitate securing an elongated member to a cranium of a patient. For example, a cranial implant is described that is configured to be partially inserted within a burr hole of the cranium and a portion of the cranial implant is configured to rest on an exterior surface of the cranium. In some examples, the cranial implant may be referred to as a burr hole plug or burr hole guide as the portion of the cranial implant configured to be inserted within the burr hole and the elongated member occupy the majority of area of the burr hole. In this manner, the cranium implant may be configured to guide the elongated member out of the burr hole and retain the elongated member at the desired circumferential location and axially with respect to the burr hole. In some examples, the elongated member may be an electrical stimulation lead coupled to an implantable stimulator or a drug deliver catheter coupled to a drug pump.

In some examples, a relatively small burr hole may be desired, where the burr hole diameter is not substantially larger than the diameter of the elongated member. Pre-procedural strategies and surgical planning may be used prior to surgery in order to know precisely where the burr hole should be created in the cranium. Therefore, a smaller burr hole may be created than typical surgeries in which a larger burr hole is needed to allow physicians flexibility in elongated member positioning. For example, before creating the burr hole with a twist drill, the clinician may conduct a pre-procedural magnetic resonance imaging (MM) scan and/or use software to create a three-dimensional delivery path plan for implanting the elongated member to the target location within the brain. Potential blood vessels along the delivery path may be discovered before creating the burr hole in the cranium so that the planned delivery path may avoid any potential problematic locations. With a delivery path that has been selected to avoid potential problems, e.g., blood vessels, the physician may utilize a small burr hole that needs only to be sized large enough to allow insertion of the elongated member to the planned target location. In other words, there may not be a need to create large burr holes that support larger implantation trajectories. In some examples, a relatively small burr hole may reduce how far the profile of the cranial implant and any accompanying device, such as a fixation cap or fixation plate, extend outward from the skull.

In some examples, the interior portion of the cranial implant that is inserted into the burr hole may have an arcuate cross-sectional shape that provides a portion that can be fit within the cylindrical burr hole. In other examples, the interior portion may provide a complete perimeter around the burr hole, such as cylindrical, triangular, rectangular, other geometric shapes. In some examples, the shape of the interior portion of the cranial implant may be selected to achieve a desired fixation force of the cranial implant within the burr hole and/or the fixation force to the lead (or other elongated member) inserted within the channel defined by the interior portion of the cranial implant. In some examples, the cylindrical shape or arcuate shape may be formed to match the curvature of a specific diameter burr hole or constructed of a material that is flexible to form to the curvature of the inside of burr holes having different diameters. The exterior portion of the cranial implant that remains external of the cranium may have a surface that approximates the curvature of the exterior of the cranium of the patient. The exterior portion of the cranial implant may form a channel through which the elongated member may reside after exiting the cranium. In some examples, the external portion of the cranial implant may have a low-profile such that the cranial implant does not extend away from the cranium much, if any, distance past the diameter of the elongated member.

In some examples, a nonmetallic (e.g., not electrically conductive) plate or cap may be used in addition to the cranial implant to secure the cranium implant and/or the elongated member to the cranium. For example, a fixation cap made of a polymer may be configured to cover and secure the cranial implant to the cranium of the patient. Since the fixation cap is not electrically conductive, the fixation cap may contribute to securing the elongated member without heating during inductive charging of a nearby IMD located on the head of the patient.

Although the cranial implant and techniques are described herein with respect to a cranium, these devices and techniques may be utilized at any anatomical location in which an elongated member needs to be secured to bone or other substantially rigid tissue.

FIG. 1 is a conceptual diagram illustrating an example system 10, in accordance with one or more aspects of this disclosure. In the example of FIG. 1, system 10 includes a cranial implant 12, a lead 14, an implantable medical device (IMD) 16, and a programmer 18. Cranial implant 12 may retain lead 14 with respect to cranium 22. Lead 14 may be implanted for a patient 20, who is ordinarily a human, at least partially through their cranium 22 via a burr hole 24 to a target site. Cranial implant 12 may be partially inserted in burr hole 24 and may be configured to secure lead 14 within burr hole 24 such that electrodes of lead 14 remain disposed at one or more target sites.

Although the techniques described in this disclosure are generally applicable to a variety of medical devices, this disclosure generally discusses techniques in the context of cranial implants securing or restraining electrical stimulation leads coupled to implantable neurostimulators for delivering deep brain stimulation (DBS) therapy. However, this disclosure may refer to a cranial implant system that may be used for many types of leads and therapies. For example, therapies may include electrical stimulation therapy to various tissue sites to treat a variety of symptoms or conditions such as chronic pain, tremors, Parkinson's disease, epilepsy, urinary or fecal incontinence, sexual dysfunction, obesity, or gastroparesis. Electrical stimulation may be used in different therapeutic applications, such as spinal cord stimulation (SCS), pelvic stimulation, gastric stimulation, or peripheral nerve field stimulation (PNFS). Cranial implant 12 may restrain lead 14 and assist in securing lead 14 longitudinally and/or circumferentially with respect to cranium 22. In other examples, cranium implants described herein may be configured to secure elongated members such as leads carrying temperature sensors, ultrasound transducers, optical fibers, or cameras, or elongated members defining one or more lumens such as a drug delivery catheter.

Cranial implant 12 may be implanted anywhere in the cranium 22 that is appropriate for insertion of lead 14 through a burr hole. Cranial implant 12 may be implanted with respect to burr holes located in approximately the same location as IMD 16. Cranial implant 12 may have a portion that is inserted within the burr hole, and a portion that remains external from the cranium. The insertable portion may be configured to guide the lead through a portion of the burr hole. For example, the insertable portion may be arcuate in shape to fit within the cylindrical burr hole. The external portion of cranial implant 12 may be coupled (e.g., formed with or attached to) the insertable portion. The external portion may define a surface that rests against the exterior surface of the cranium 22 and define a channel through which the lead 14 may be retained as lead 14 exits from burr hole 24.

In some examples, a clinician may create burr hole 24 in cranium 22 using a twist drill loaded on a frame. Clinicians may use twist drills for creating burr holes 24 with varying diameters, e.g., burr holes having a range of between approximately 2 millimeters (mm) and approximately 14 mm, and more specifically a range of between approximately 3 mm and approximately 6 mm. In some examples, cranial implant 12 may be flexible in order to fit within burr holes having this range of diameters and provide a friction fit within the burr hole. In other examples, different sized cranial implants may be formed to fit within respective burr hole sizes. In this manner, cranial implant 12 may be adapted to fit a range of diameters of burr hole 24.

Cranial implant 12 may be used to retain lead 14 anywhere on the path of the leads 14 between the therapy delivery site and IMD 16. Although lead 14 is coupled to IMD 16 disposed on cranium 22 of patient 20, lead 14 may extend to IMD 16 implanted anywhere in the head or torso including, for example, leads 14 running along the surface of the skull, running beneath the skull such as near or on the dura mater, placed adjacent cranial or other nerves in the head, or placed directly on the surface of the brain. In other examples, IMD 16 may be implanted anywhere within patient 20 (e.g., near the abdominal region or near the pectoral region). Lead 14 may extend from IMD 16 through a burr hole 24 to a target site in the brain of patient 20, including tunneling through tissue of the brain of patient 20.

In some examples, cranial implant 12 may be formed of materials configured to retain lead 14 for as long as lead 14 remains implanted within patient 20. Lead 14 and IMD 16 may remain implanted within patient 20 for weeks, months, or years. Consequently, cranial implant 12 may need to remain implanted in burr hole 24 and retain lead 14 for the same amount of time. In some examples, cranial implant 12 may be made of a material that is biocompatible with patient 20 for these durations. In other examples, cranial implant 12 may be configured to biodegrade over time because tissue growth around lead 14 may encapsulate lead 14 without the need for cranial implant 12.

In some examples, as shown in FIG. 1, cranial implant 12 may rely on friction to appropriately retain lead 14 within burr hole 24. In this manner, cranial implant 12 may use an interference fit to remain in burr hole 24. The portion of cranial implant 12 that is inserted within burr hole 24 may be sized to match the diameter of the burr hole or the insertable portion of cranial implant 12 may provide a bias against the wall of burr hole 24. In other examples, one or more ribs may provide an interference fit on the insertable portion of cranial implant 12. In some examples, cranial implant 12 may utilize at least one of a fixation member, e.g. a fixation cap or a fixation plate, bone cement, and an interference fit to both retain lead 14 and secure cranial implant 12 to cranium 22 of patient 20.

In some examples, one or more leads 14 of system 10 may include a lead extension or other segments that may aid in implantation or positioning of lead 14. Lead 14 may include a plurality of electrodes, and IMD 16 may deliver stimulation to the brain of patient 20 via the electrodes. IMD 16 may be coupled to any number of leads 14. Cranial implant 12 may retain one or more leads 14 in some examples. A proximal end of lead 14 may include a connector (not shown) that electrically couples to a header of IMD 16. In some examples, IMD 16 may be coupled to two leads 14 that extend through only one burr hole 24 in cranium 22 or extend through separate respective burr holes 24 in cranium 22 (e.g., to access separate hemispheres of the brain of patient 20).

In some examples, lead 14 and/or a lead extension may be sized in order to be able to reach the target site within cranium 22 and reach the location where IMD 16 is implanted. In some examples, IMD 16 may be located far from burr hole 24 and lead 14 delivery site may be located deep within cranium 22. In other examples, IMD 16 may be located close to burr hole 24 and may not need to extend far into cranium 22 to reach the delivery site. Cranial implant 12 and/or a fixation cap attachable to cranial implant 12 may provide one or more structures that retain excess length of lead 14 when lead 14 is longer than the distance between the target implant site and the location of IMD 16.

In some examples, lead 14 may include one or more electrodes that are implanted or otherwise placed adjacent to the target tissue. One or more electrodes may be disposed at a distal tip of lead 14 and/or at other positions at intermediate points along lead 14. Electrodes of lead 14 may transfer electrical stimulation (e.g., as generated by an electrical stimulation generator in IMD 16) to tissue of patient 20. The electrodes may be electrode pads on a paddle lead, circular (e.g., ring) electrodes surrounding the body of the lead, conformable electrodes, cuff electrodes, segmented electrodes (e.g., multiple electrodes located at the same axial location of the lead but different circumferential locations of the lead), or any other type of electrodes capable of forming unipolar, bipolar or multipolar electrode configurations for therapy. In general, ring electrodes may be arranged at different axial positions at the distal ends of lead 14.

Using such electrodes of lead 14, IMD 16 may deliver electrical stimulation energy (e.g., current or voltage-based pulses) to the one or more targeted locations within patient 20 according to one or more therapy/stimulation program. In some examples, IMD 16 may deliver stimulation to the brain of patient 20 to provide DBS therapy or to stimulate the cortex of the brain. IMD 16 may be used to treat any nervous system disorder including, but not limited to, epilepsy, pain, psychological disorders including mood and anxiety disorders, movement disorders (MVD), such as, but not limited to, dystonia, essential tremor, Parkinson's disease, and neurodegenerative disorders.

Although lead 14 is described as generally delivering or transmitting electrical stimulation signals, lead 14 may additionally or alternatively transmit electrical signals from patient 20 to IMD 16 for monitoring. Alternatively, or additionally, lead 14 and IMD 16 may be configured to provide other types of therapy through the delivery of a therapeutic agent to the target tissue of patient 20. For example, IMD 16 may additionally or alternatively deliver a therapeutic agent such as a pharmaceutical, biological, or genetic agent. In these examples, lead 14 may function as a catheter or IMD 16 may be otherwise coupled to a catheter. Cranial implant 12 may retain lead 14 when lead 14 functions as a catheter.

A user, such as a clinician or patient 20, may interact with a user interface of an external programmer 22 to program IMD 16. Programming of IMD 16 may refer generally to the generation and transfer of commands, programs, or other information to control the operation of IMD 16. For example, programmer 18 may transmit programs, parameter adjustments, program selections, group selections, or other information to control the operation of IMD 16, e.g., by wireless telemetry or wired connection. In some examples, programmer 18 may be primarily intended for use by a clinician, a patient, or both. In some examples involving an IMD 16 having a rechargeable power source, a user(s) may program and charge IMD 16 using one device that serves as both a recharger and a programmer. In other such cases, multiple devices may be used for these functions (e.g., a separate recharger and one or more programmers 18.)

Cranial implant 12 and IMD 16 may be constructed of any polymer, metal, or composite material suitable for being implanted within patient 20. However, when cranial implant is intended to be implanted near IMD 16 on cranium 22, cranial implant 12 may be constructed out of polymers or other non-electrically conductive materials in order to prevent eddy currents and heating during wireless charging of IMD 16. In some examples, cranial implant 12 may be constructed with a ceramic or a biocompatible polymeric material, such as nylon, silicone, polyurethane, polyether ether ketone (PEEK), or low-density polyethylene (LDPE), or a combination thereof. Although cranial implant 12 may be constructed of a unitary material, cranial implant 12 may be made out of two or more materials in other examples. For example, cranial implant 12 may be constructed of a relatively flexible portion that is inserted in patient 20 and a relatively rigid portion that remains external from cranium 22 that is used to retain lead 14. An example of cranial implant 12 is shown in greater detail in FIG. 3. Materials and construction of cranial implant 12 of this disclosure may be selected such that cranial implant 12 is MRI compatible (e.g., cranial implant 12 can be within the magnetic field and electrical fields of an MRI machine with substantially no damage to cranial implant 12, the MRI device, or impacts to patient 20).

Figure 2:
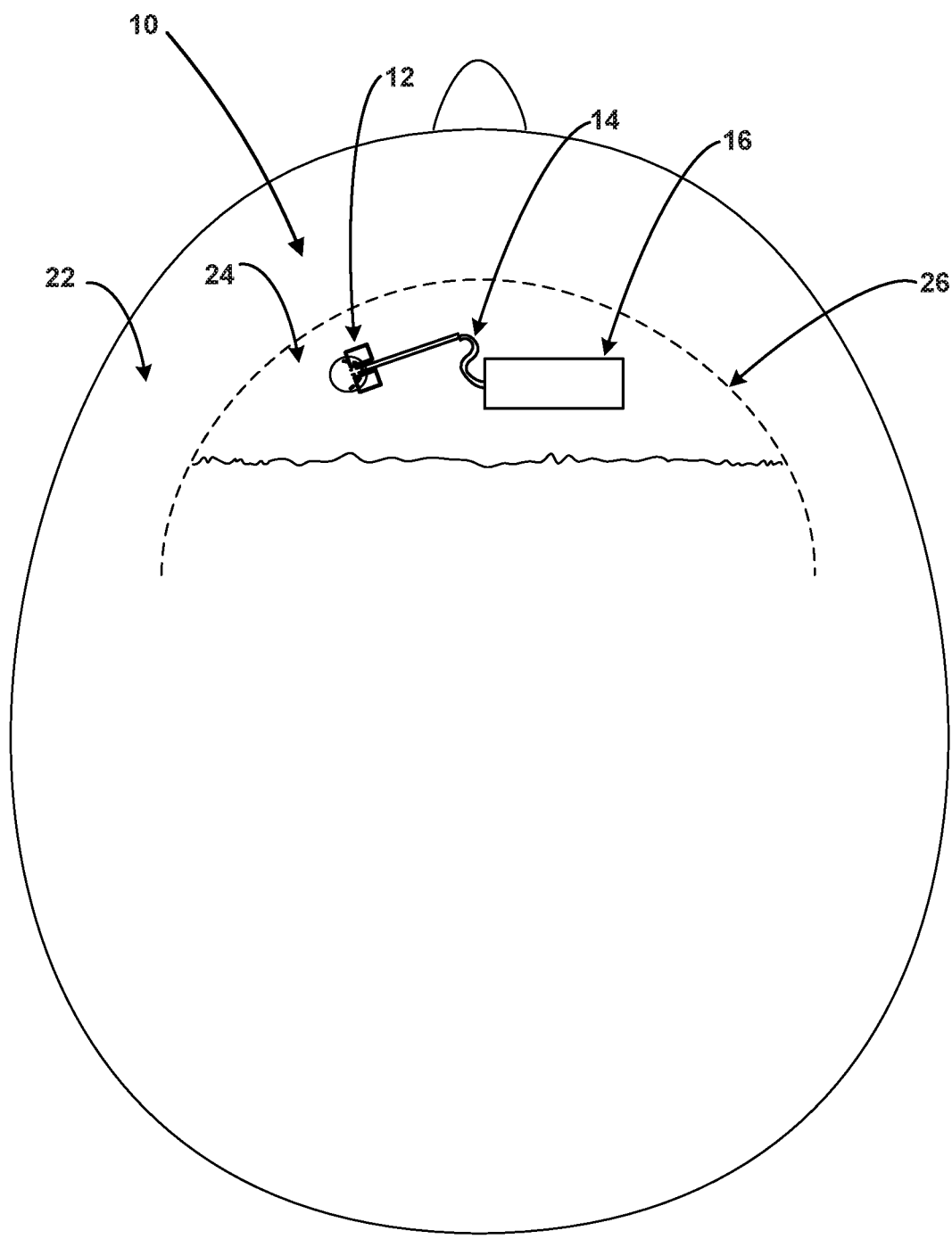
FIG. 2 is a conceptual diagram illustrating a top view of the example cranial implant system of FIG. 1.

FIG. 2 is a conceptual diagram illustrating example cranial implant system 10, in accordance with one or more aspects of this disclosure. In some examples, cranial implant 12 of cranial implant system 10 may be implanted in burr hole 24 of patient 20. The location on cranium 22 at which cranial implant 12 and IMD 16 are illustrated in FIG. 2. However, cranial implant 12 and IMD 16 may be implanted anywhere on the surface of cranium 22. In some examples, two burr holes are created in cranium 22 above respective hemispheres of the brain. In order to make burr hole 24 and implant cranial implant 12 on cranium 22, a clinician may make an incision 26 through the scalp of patient 20 and pull back a resulting flap of skin to expose the desired area of cranium 22. Incision 26 may, as shown in FIG. 2, be generally shaped like a "C." Such an incision is commonly referred to as a "C-flap" incision. However, other procedures may be used to expose cranium 22 for creation of burr hole 24.

Burr hole 24 may be created by drilling through cranium 22, after which lead 14 may be inserted through burr hole 24 and into the brain of patient 20. As discussed above, in examples where system 10 includes more than one lead 14, more than one burr hole 24 may be created in cranium 22. One or more leads 14 may be connected to IMD 16, either directly or via a lead extension, and IMD 16 may be placed at least partially within a pocket or recess formed using a hand or a tool beneath the scalp adjacent burr hole(s) 24. In some examples, IMD 16 is placed entirely or partially within the recess created in cranium 22. This recess may allow the housing of IMD 16 to lie at least partially within cranium 22 and reduce a profile, or height, of IMD 16 relative to the outside surface of cranium 22.

Figure 3:
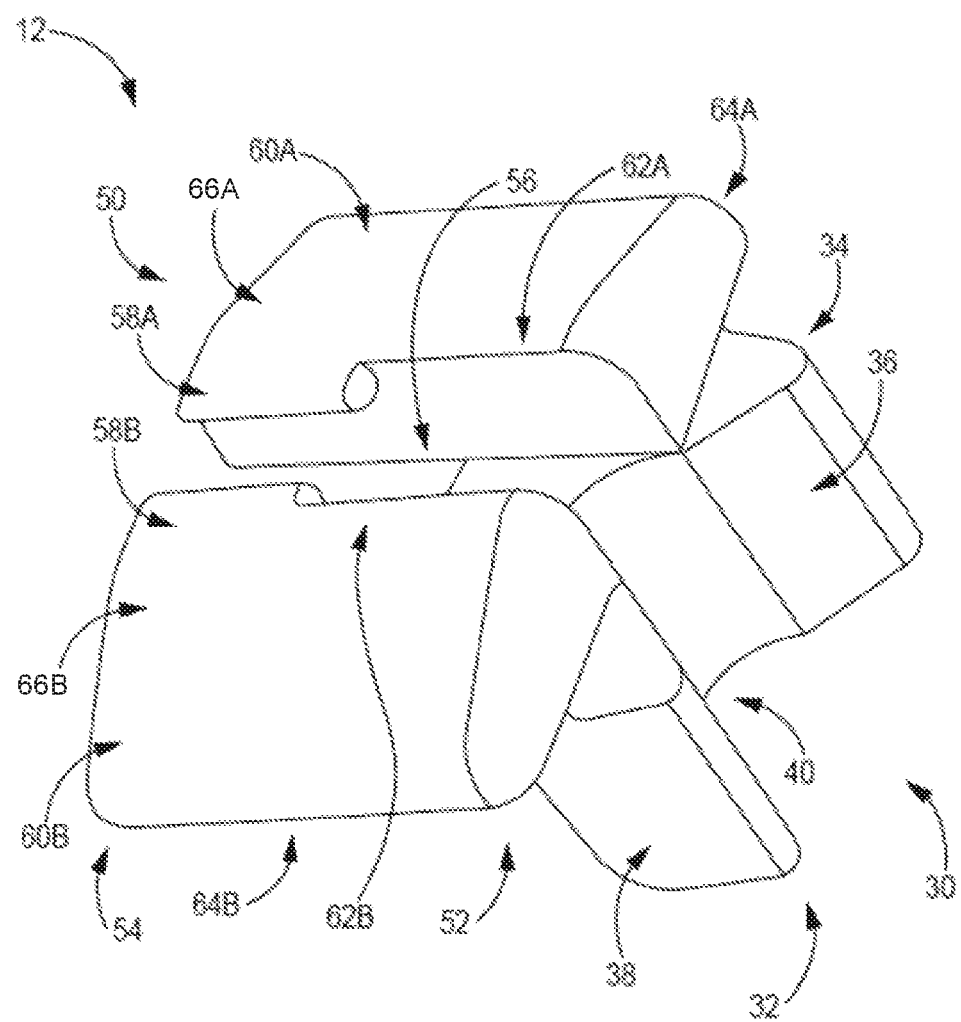
FIG. 3 is a perspective view of an example cranial implant configured to secure an elongated member to a cranium.

FIG. 3 is a conceptual diagram illustrating example cranial implant 12, in accordance with one or more aspects of this disclosure. In some examples, cranial implant 12 may include an arcuate guide portion 30 and an exterior guide portion 50. In some examples, arcuate guide portion 30 may include a distal end 32, a proximal end 34, an inner surface 36, an outer surface 38, wherein the inner surface defines a first channel 40. In some examples, exterior guide portion 50 may define a distal cranially facing surface 52, a proximal cranially facing surface 54, which both are under the view of exterior guide portion 50. Exterior guide portion 50 may also include inner edge segments 62A and 62B which define a second channel 56. Exterior guide portion 50 may also include flanges 58A and 58B that also partially define the second channel 56. Arcuate guide portion 30 of cranial implant 12 may be constructed of a first material and exterior guide portion 50 of cranial implant 12 may be constructed of a second material. The first material may be the same or different than the second material. As shown in FIG. 3, exterior guide portion 50 is coupled to, attached to, or formed with, arcuate guide portion 30.

In some examples, arcuate guide portion 30 may have an inner diameter range of between approximately 0.762 millimeters (mm) (0.030 inches (in)) and approximately 2.032 mm (0.080 in), an outer diameter range of between approximately 1.778 mm (0.070 in) and approximately 15.240 mm (0.600 in), and extend into the skull a depth in the range of between approximately 1.016 mm (0.040 in) and approximately 7.620 mm (0.300 in). In some examples, exterior guide portion 50 may have a distance between inner edge segments 62A and 62B in the range of between approximately 5.080 mm (0.020 in) and approximately 1.778 mm (0.070 in), a height of exterior guide portion 50 above skull in the range of between approximately 0.762 mm (0.030 in) and approximately 2.540 mm (0.100 in), and a length of exterior guide portion 50 in the range of between approximately 1.270 mm (0.050 in) and approximately 15.240 mm (0.600 in).

Arcuate guide portion 30 may be configured to be disposed in burr hole 24 of cranium 22. Distal end 32 may be inserted further into burr hole 24 than proximal end 34. Inner surface 36 may at least partially define first channel 40, which is configured to receive and retain an elongated member, such as a catheter or lead 14. In some examples, outer surface 38 may be configured to extend around varying amount of the circumference of burr hole 24, such as less than the full circumference of burr hole 24 or up to the full circumference of burr hole 24. In one example, outer surface 38 of arcuate guide portion 30 may face a radially outward direction from first channel 40 and may be substantially coaxial with inner surface 36 of arcuate guide 30. In some examples, outer surface 38 of arcuate guide portion 30 may be aligned along a different axis than inner surface 36 of arcuate guide 30. Inner surface 36 may include a curved portion of first channel 40, wherein the curved portion connects two flat portions closer to the outward edge of arcuate guide portion 30. In other examples, inner surface may include additional shaped portions creating different curved shapes or may only define a single continuous curve. Alternatively, inner surface 36 may define two connecting flat surfaces which meet to create a "V" shaped channel 40.

In some examples, distal cranially facing surface 52 of exterior guide portion 50 is coupled to proximal end 34 of arcuate guide portion 30 and may extend over burr hole 24. Proximal cranially facing surface 54 of exterior guide portion 50 may contact the external surface of cranium 22 away from burr hole 24.

Exterior guide portion 50 may be coupled to arcuate guide portion 30 and remain external of cranium 22 and may contact an external surface of cranium 22. Second channel 56, like first channel 40, may receive and retain an elongated member, such as a catheter or lead 14. In some examples, one or more flanges 58A and 58B may be coupled to or formed from exterior guide portion 50 and may retain lead 14 at least partially within second channel 56. In some examples, one or more flanges 58A and 58B may enable lead 14 to snap or rest in place in second channel 56 of exterior guide portion 50.

In some examples, exterior guide portion 50 may extend radially outward from the center axis of first channel 40. Exterior guide portion 50 may extend in one direction from first channel 40, such as the direction in which the elongated member will extend out of the burr hole. In this manner, exterior guide portion 50 would not encircle the burr hole. However, in some examples, exterior guide portion 50 may extend circumferentially partially around the burr hole. Exterior guide portion 50 may extend varying amounts over burr hole 24. In some examples, exterior guide portion 50 may extend over less than the full circumference of burr hole 24. In other examples, exterior guide portion 50 may be configured to extend over the full the circumference of burr hole 24.

In some examples, exterior guide portion 50 may also include a first wing segment 60A and a second wing segment 60B. First wing segment 60A may include an inner edge 62A, an outer edge 64A, and an exterior facing surface 66A. Similarly, second wing segment 60B may include an inner edge 62B, an outer edge 64B, and an exterior facing surface 66B. In some examples, first wing segment 60A and second wing segment 60B may be coupled to arcuate guide portion 30. First wing segment 60A and second wing segment 60B may extend radially outward from proximal end 34 of arcuate guide portion 30. In some examples, opposing surfaces of first wing segment 60A and second wing segment 60B may at least partially define second channel 56.

One or more flanges 58A and 58B may extend varying amounts along inner edge 62A and inner edge 62B. In the example of FIG. 3, flanges 58A and 58B extend less than half the length of inner edge 62A and inner edge 62B, respectively. In some examples, one or more flanges 58A and 58B may extend the full length or longer along inner edge 62A and inner edge 62B, respectively. In one example, one or more flanges 58A and 58B may extend less than the full length of inner edge 62A and inner edge 62B and may be located along any portion of inner edge 62A and inner edge 62B, respectively. In some examples, flanges 58A and 58B may extend along substantially similar portions of their respective inner edges 62A and 62B, or flanges 58A and 58B may extend along different portions of their respective inner edges 62A and 62B, respectively.

Flange 58A and inner edge 62A of first wing segment 60A may form a substantially continuous surface. Likewise, flange 58B and inner edge 62B of second wing segment 60B may form a substantially continuous surface. The substantially continuous surfaces of first wing segment 60A and second wing segment 60B may be planar, have a curvature, or may be a series of relatively flat surfaces connected at an angle.

Figure 4:
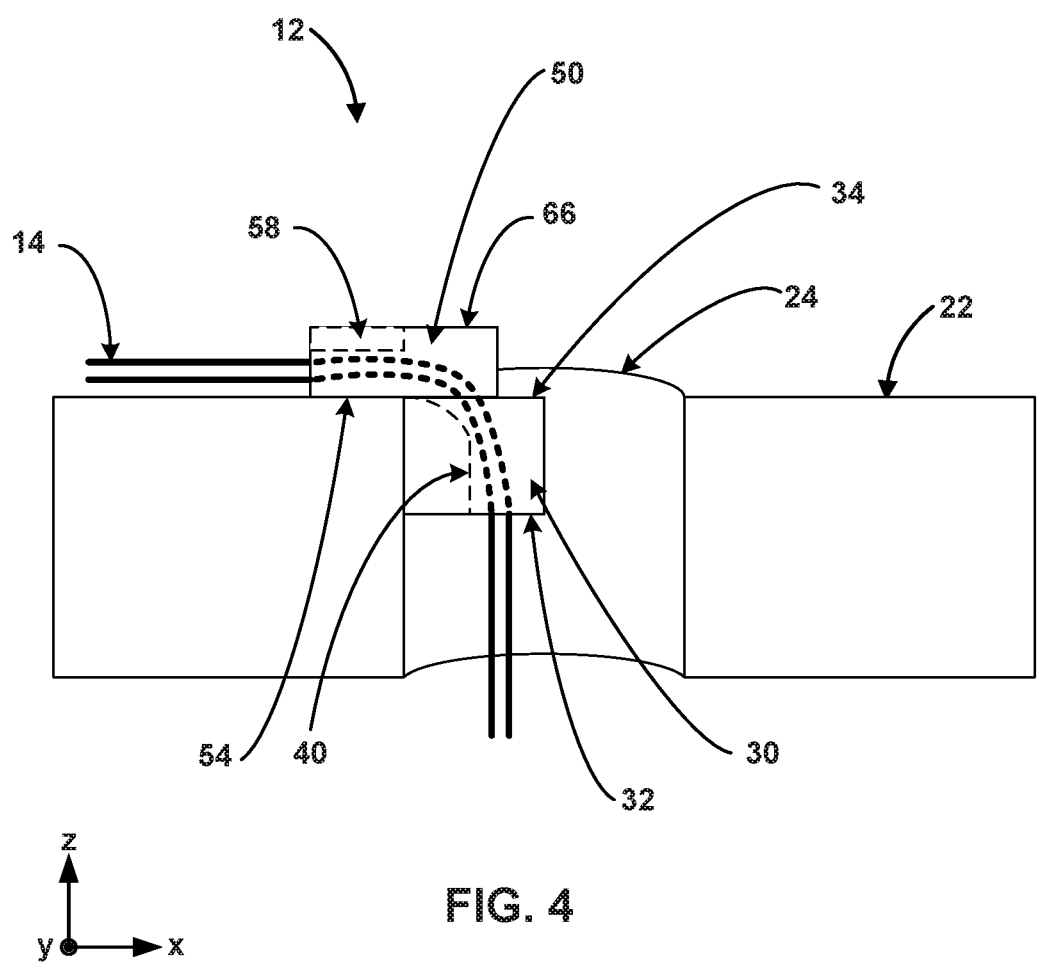
FIG. 4 is a cross-sectional view of an example cranial implant.

In some examples, first channel 40 may define a center axis, and likewise, second channel 56 may define a center axis. In some examples, an angle may be defined between the center axis of first channel 40 and the center axis of second channel 56. FIGS. 3 and 4 show the angle as substantially orthogonal, or approximately 90 degrees, but the angle may be less than 90 degrees or greater than 90 degrees in other examples. In some examples, an angle between first channel 40 and second channel 56 may be based on factors for retaining cranial implant 12 in burr hole 24. In some examples, the connection between first channel 40 and second channel 56 may define a curvature that provides strain relief to the elongated member. FIG. 3 shows first channel 40 disposed along the center axis of arcuate guide portion 30, and likewise, second channel 56 disposed along the center axis of exterior guide portion 50. In some examples, first channel 40 and second channel 56 may be disposed offset from their respective center axis.

Generally, arcuate guide portion 30 may be constructed of a continuous material. In other examples, a hinge (not shown) may be added to arcuate guide portion 30. The hinge may allow a portion of arcuate guide portion 30 to fold in and out so that cranial implant 12 may expand or contract to accommodate varying curvatures of different sizes of burr hole 24. In some examples, the distance between inner surface 36 and outer surface 38 of arcuate guide portion 30 may gradually decrease (e.g., become thinner) moving in a circumferentially outward direction from first channel 40 to the outer edges of arcuate guide portion 30 where inner surface 36 and outer surface 38 meet. The decreasing thickness of arcuate guide portion 30 may make arcuate guide portion 30 progressively more flexible in an outwardly direction from first channel 40 to where inner surface 36 and outer surface 38 meet. In some examples, different portions of arcuate guide portion 30 may be made of different material. In one example, the outer edges of arcuate guide portion 30 where inner surface 36 and outer surface 38 meet may be made of a more flexible material than the material located proximate to first channel 40. By making the outer edges of arcuate guide portion 30 more flexible, arcuate guide portion 30 may have a more secure fit within burr hole 24. In addition, arcuate guide portion 30 may promote retaining the elongate member towards the center of the burr hole. Although cranial implant 12 is described as having two different portions, cranial implant 12 may be a continual structure with no clear delineation between insertable (arcuate guide portion 30) and external (external guide portion 50) portions.

FIG. 4 is a conceptual diagram illustrating example cranial implant 12, in accordance with one or more aspects of this disclosure. As shown in the example of FIG. 4, flanges 58, second channel 56 (not shown), and first channel 40 may provide a path for lead 14 to travel from outside cranium 22 through burr hole 24 to a delivery site within cranium 22. Arcuate guide portion 30 and exterior guide portion 50 may be constructed with difference sizes along the x-, y-, and z-dimensions of FIG. 4 to provide a secure fit for cranial implant 12 in different sizes of burr hole 24. In some examples, arcuate guide portion 30 may stay the same size over a range of burr hole 24 diameters and exterior guide portion 50 may increase in size as burr hole 24 increases in size so that proximal cranially facing surface 54 may remain on an exterior of burr hole 24 and provide a lip or flange to prevent cranial implant 12 from descending too far into burr hole 24. In contrast, in some examples, arcuate guide portion 30 may vary in size over a range of burr hole 24 diameters and exterior guide portion 50 may remain the same size. In some examples, distal end 32 of arcuate guide portion 30 may extend to different depths into burr hole 24 along a z-dimension.

In some examples, more than one exterior guide portion 50, or a larger exterior guide portion 50, may be coupled to arcuate guide portion 30. Burr hole 24 with a large diameter may require more than one exterior guide portion 50 to keep cranial implant 12 from extending too far into burr hole 24. In some examples, more than one lead 14 may be delivered into one burr hole 24. More than one lead 14 may be managed by one exterior guide portion 50 and inserted into second channel 56 and delivered to the target site. Or, each lead 14 may be managed by their own respective exterior guide portion 50, which are all coupled to one arcuate guide portion 30 and delivered to a target site within cranium 22. In some examples, more than one cranial implant 12 may be inserted into one burr hole 24.

Although exterior guide portion 50 is shown as having a larger thickness than the diameter of lead 14, the thickness of exterior guide portion 50 may be similar to the diameter of lead 14 in other examples to limit the profile of cranial implant above the exterior surface of cranium 22. For example, exterior guide portion 50 may include ramped flanges 58 to follow the curvature of lead 14. In other examples, exterior guide portion 50 may be configured to capture only the sides of lead 14 such that the thickness of exterior guide portion 50 in the Z-dimension is less than the diameter of lead 14.

Figure 5A:
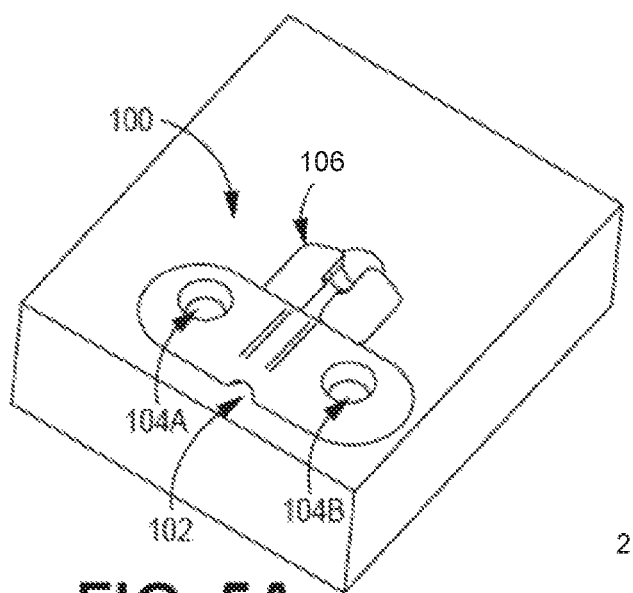
FIG. 5A is a conceptual diagram illustrating an example cranial implant and a fixation plate, in accordance with one or more aspects of this disclosure.

FIG. 5A is a conceptual diagram illustrating an example fixation plate 100, in accordance with one or more aspects of this disclosure. A fixation plate 100, as shown in FIG. 5A, may be disposed on cranium 22 adjacent an exterior portion of cranial implant 106 (which may be similar to cranial implant 12). In some examples, fixation plate 100 and cranial implant 106 may be touching when implanted. Fixation plate 100 may define a channel to guide lead 14 and may secure lead 14 and/or cranial implant 106 in burr hole 24. Fixation plate 100 may have a third channel 102 on the underside so that a bottom portion of fixation plate 100 may remain flush with cranium 22 while fixation plate 100 is covering and guiding lead 14. Similar to IMD 16 as described above, by fixation plate 100 remaining flush to an outside surface of cranium 22, fixation plate 100 may have a reduced outer surface profile relative to the outside surface of cranium 22. Configuring the outside surface of fixation plate 100 to approximate the curvature of cranium 22 may reduce the profile of fixation plate 100 and/or may increase how securely fixation plate 100 may be attached to cranium 22. In some examples, the more secure fixation plate 100 is secured to cranium 22, the more secure cranial implant 106 and lead 14 will be. In some examples, fixation plate 100 may help secure lead 14 in second channel 56 of exterior guide portion 50.

In some examples, fixation plate 100 may be made of the same materials as cranial implant 12 as described above. In one example, fixation plate 100 may be made of more than one material. For example, a ring of more rigid material may surround each of screw openings 104A and 104B. The more rigid material surrounding screw openings 104A and 104B may resist deformation from pressure applied by bone screws keep fixation plate 100 secure to cranium 22 while not allowing the bone screws to damage fixation plate 100.

Figure 5B:
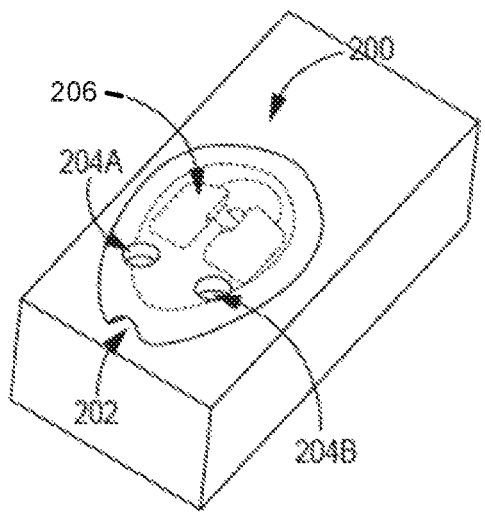
FIG. 5B is a conceptual diagram illustrating an example cranial implant and an example fixation cap, in accordance with one or more aspects of this disclosure.

FIG. 5B is a conceptual diagram illustrating an example fixation cap 200, in accordance with one or more aspects of this disclosure. Similar to fixation plate 100, fixation cap 200 may define a third channel 202 disposed on the underside of fixation cap 200 so that a bottom portion of fixation cap 200 may remain flush with cranium 22 while fixation cap 200 is covering and directing lead 14. In addition, fixation cap 200 may extend over a portion or the entire burr hole 24. Similar to fixation plate 100 described above, by fixation cap 200 remaining flush to an outside surface of cranium 22, fixation cap 200 may have a reduced outer surface profile relative to the outside surface of cranium 22. Configuring the outside surface of fixation cap 200 to approximate the curvature of cranium 22 may reduce the profile of fixation cap 200 and/or may increase how securely fixation cap 200 may be attached to cranium 22. Since cranial implant 206 may not include its own fixation mechanism, fixation cap 200 may function to secure cranial implant 206 and lead 14.

Similar to fixation plate 100 described above, fixation cap 200 may be made of the same materials as cranial implant 12 as described above. In one example, fixation cap 200 may be made of more than one material. For example, the material surrounding screw openings 204A and 204B may be made of a more rigid material to help ensure the integrity of screw openings 204A and 204B.

Figure 5C:
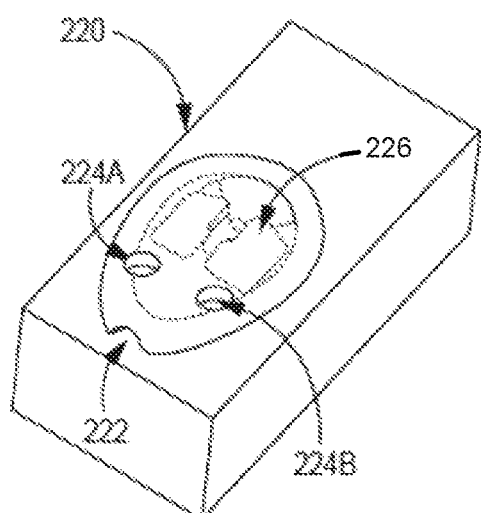
FIG. 5C is a conceptual diagram illustrating an example cranial implant and an example fixation cap, in accordance with one or more aspects of this disclosure.

FIG. 5C is a conceptual diagram illustrating an example fixation cap 220, in accordance with one or more aspects of this disclosure. A fixation cap 220 may be similar to fixation cap 200 from FIG. 5B including screw openings 224A and 224B and a third channel 222 being the same as screw openings 204A and 204B and third channel 202, respectively. One difference between FIGS. 5B and 5C may be that cranial implant 226 is larger and is inserted in a larger burr hole than cranial implant 206, which may be inserted in a smaller burr hole. Consequently, since fixation caps 200 and 220 may be the same size in some examples, FIGS. 5B and 5C illustrate that fixation caps 200 and 220 may be the same size but configured to accept and/or cover varying sizes of cranial implants, e.g., 206 and 226, and burr holes.

Figure 6:
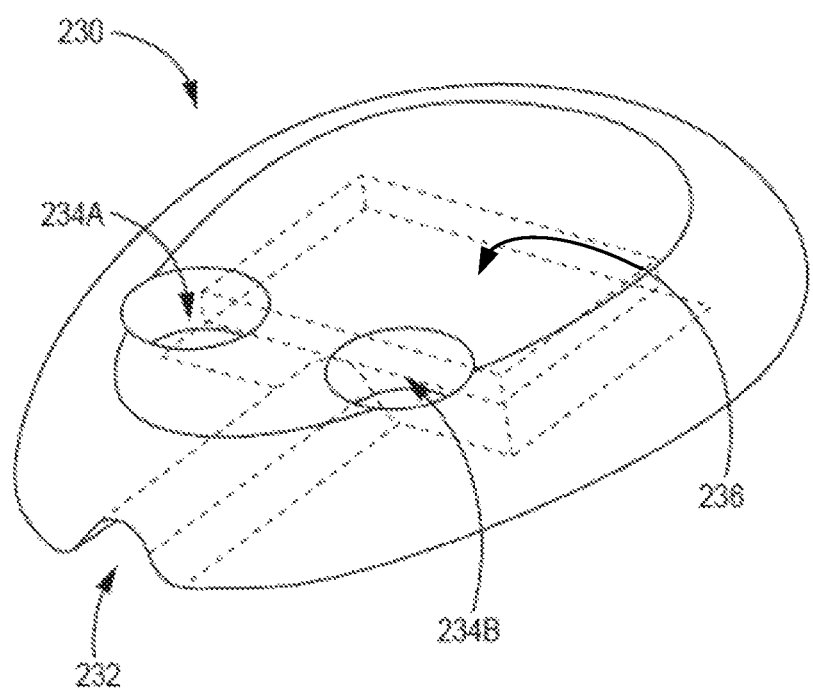
FIG. 6 is a conceptual diagram illustrating an example fixation cap, in accordance with one or more aspects of this disclosure.

FIG. 6 is a conceptual diagram illustrating an example fixation cap 230, in accordance with one or more aspects of this disclosure. A fixation cap 230 may be similar to fixation caps 200 and 220. In one example, fixation cap 230 may have a third channel 232, define screw openings 234A and 234B, and define a recess opening 236 (shown by dotted lines). In some examples, fixation cap 230 may contact cranium 22 and may define recess opening 236 that accepts the exterior guide portion of a cranial implant, e.g., exterior guide portion 50 of cranial implant 12. Third channel 232, in one example, may accept a portion of lead 14 extending out from second channel 56 of exterior guide portion 50. In some examples, third channel 232 may be shaped to provide strain relief for lead 14. For example, third channel 232 may have a curved opening so that lead 14 does not extend around a sharp corner if lead 14 is being wrapped around an exterior of fixation cap 230 or lead 14 needs to be curved en route to the implanted IMD. By third channel 232 providing strain relief based on at least partially the geometry of its opening, third channel 232 may help preserve the integrity of lead 14.

In some examples, recess opening 236 may be sized to accommodate cranial implants of varying sizes. By recess opening 236 being able to cover cranial implants of varying sizes, the same fixation cap, e.g., fixation cap 230, may be used with burr holes of varying diameters. Recess opening 236 may have a height that is common to cranial implants such that fixation cap 230 applies pressure to external guide portion 50, for example, but the width of recess opening 326 may be larger than available cranial implant sizes.

Figure 7A:
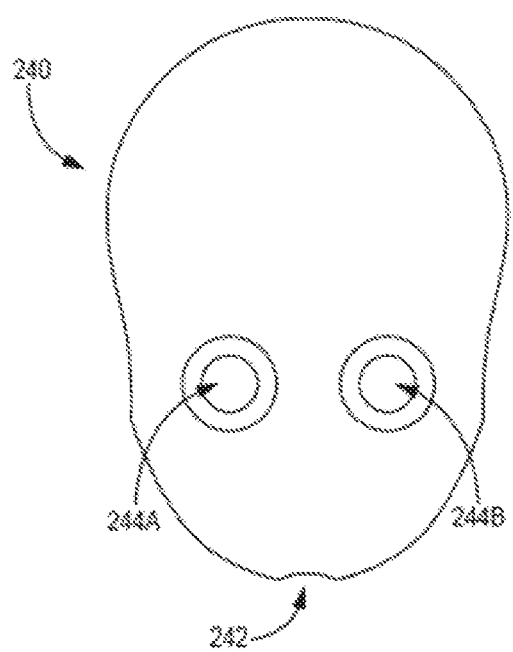
FIG. 7A is a top view of an example fixation cap, in accordance with one or more aspects of this disclosure.
Figure 7B:
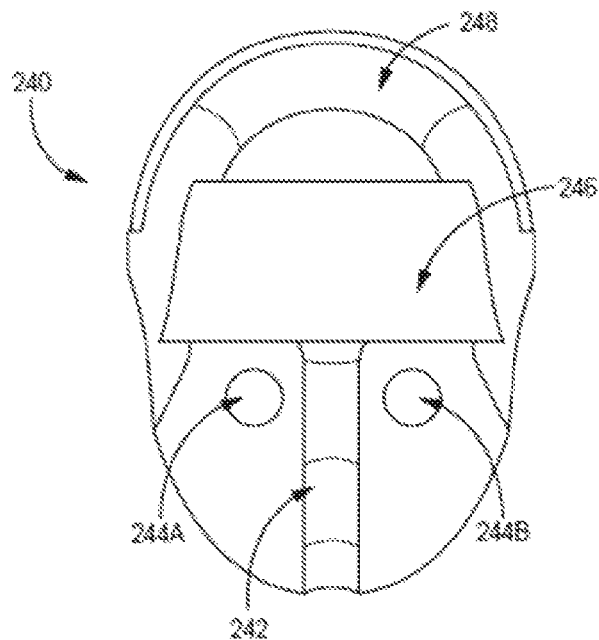
FIG. 7B is a bottom view of an example fixation cap, in accordance with one or more aspects of this disclosure.

FIGS. 7A and 7B are conceptual diagrams illustrating an example fixation cap 240, in accordance with one or more aspects of this disclosure. In some examples, fixation cap 240 may be similar to fixation caps 200, 220, and 230. Fixation cap 240 may define screw holes 244A and 244B and also define channel 242 through which the elongated member may exit the burr hole. In order to manage excess length of lead 14, fixation cap 240 may be configured to cover cranial implants, e.g., cranial implant 12. FIG. 7A shows a top perspective of fixation cap 240, and FIG. 7B shows a bottom perspective of fixation cap 240. The underside of fixation cap 240, as shown in FIG. 7B, may define a curved track 248 configured to accept lead 14 and manage excess length of lead 14. Excess length of lead 14 may be wrapped within track 248 and around fixation cap 240 so that excess length of lead 14 does not remain loose on the outside of cranium 22. In some examples, lead 14 may have a decreased chance of becoming entangled or damaged because fixation cap 240 provides a protective covering for lead 14. In some examples, more than one track (not shown) may be disposed on the underside of fixation cap 240, e.g., one track accepts a single diameter of lead 14 such that lead 14 can be wrapped multiple times around fixation cap 240 is necessary. For example, excess length of lead 14 may be wound around two track portions.

Figure 8:
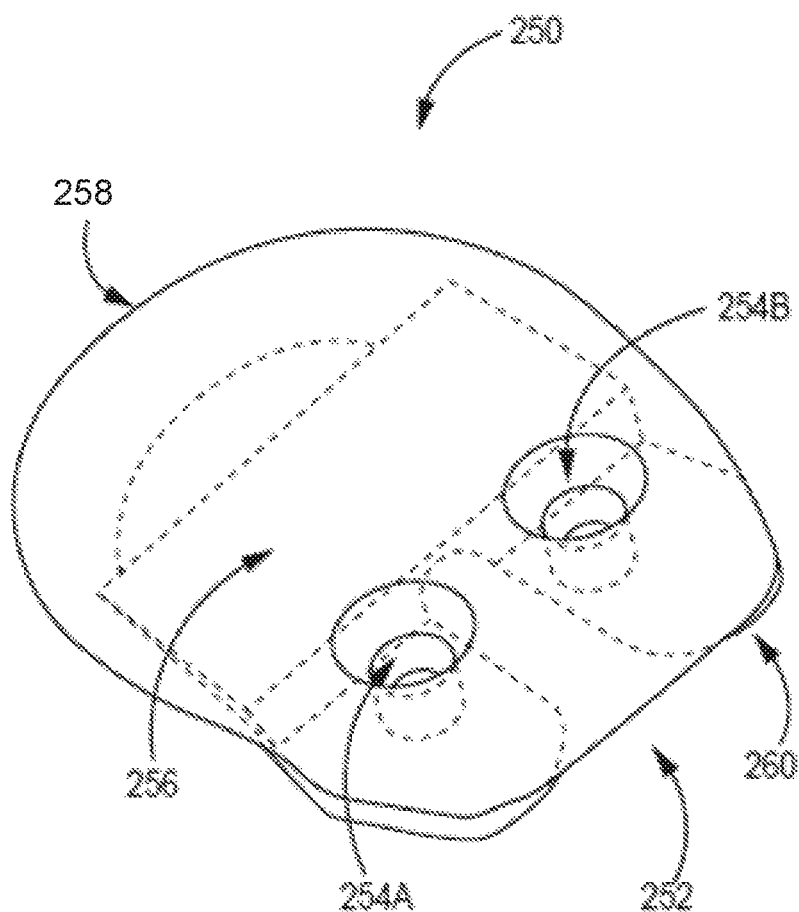
FIG. 8 is a perspective view of an example fixation cap, in accordance with one or more aspects of this disclosure.

FIG. 8 is a conceptual diagram illustrating an example fixation cap 250, in accordance with one or more aspects of this disclosure. In some examples, a fixation cap 250 may be the same as fixation caps 200, 220, 230, and 240. Fixation cap 250, in one example, may define a third channel 252, define screw openings 254A and 254B, define recess opening 256, and include a distal lip 258 and proximal lip 260. Similar to FIG. 7B where fixation cap 240 manages excess length of lead 14, fixation cap 250 may manage excess length of lead 14. However, unlike fixation cap 240 where the excess length of lead 14 is disposed on the underside of fixation cap 240, fixation cap 250 may wrap excess length of lead 14 around the exterior of fixation cap 250. In some examples, distal lip 258 and proximal lip 260 may be disposed on the exterior of fixation cap 250. Third channel 252 may reduce stress on lead 14 by providing curved surfaces for lead 14 to exit and wrap around fixation cap 250. For example, when lead 14 is wrapped around the exterior of fixation cap 250, sharp edges on third channel 252 may damage lead 14. In some examples, a track (not shown) may be disposed on the underside of fixation cap 250 in the same manner as fixation cap 240 providing lead 14 two locations to wrap excess length of lead 14.

Figure 9:
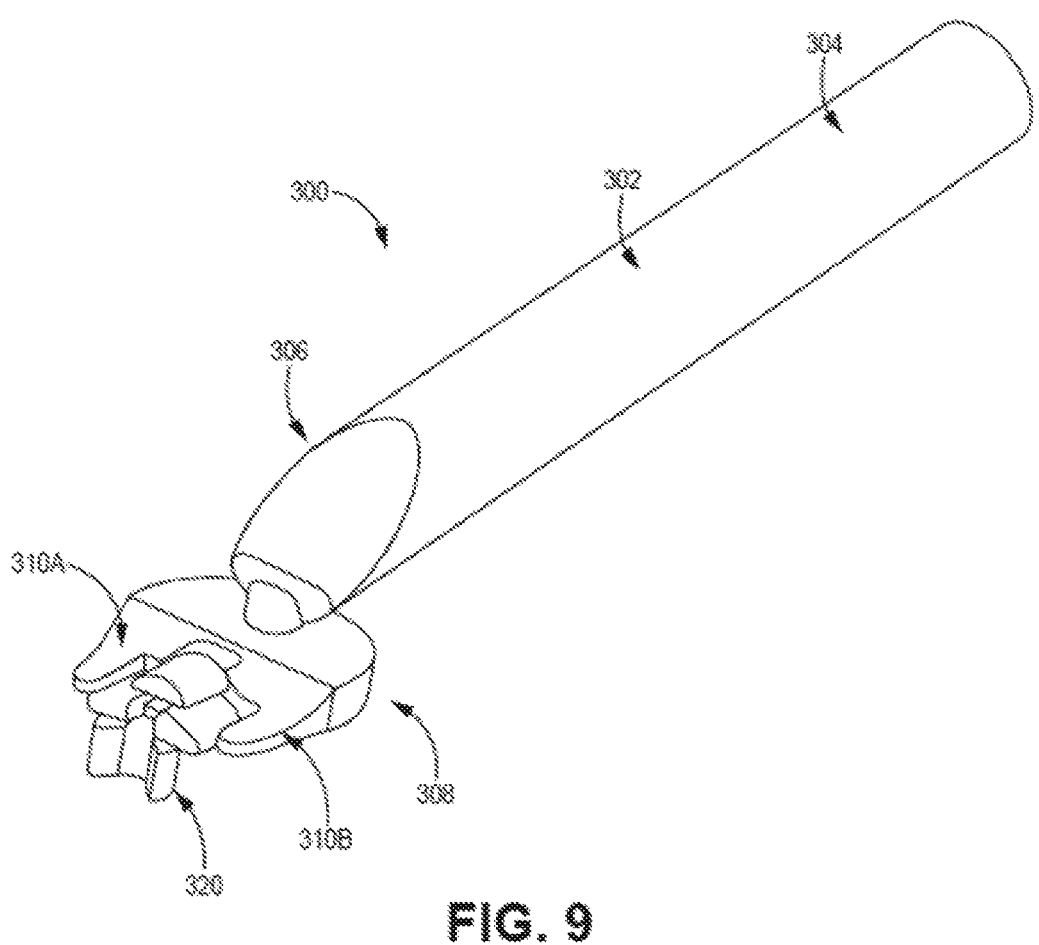
FIG. 9 is a conceptual diagram illustrating an example insertion tool configured to facilitate delivery of a cranial implant holding an example cranial implant, in accordance with one or more aspects of this disclosure.

FIG. 9 is a conceptual diagram illustrating an example insertion tool 300 for delivering a cranial implant (e.g., cranial implant 12), in accordance with one or more aspects of this disclosure. Insertion tool 300 may include a handle 302, a dispenser head 308, and be configured to attach to cranial implant 320. In some examples, cranial implant 320 may be the same or similar to cranial implant 12. Handle 302 may include various cross-sectional geometries, including, but not limited to, circular, oval, rectangular, triangular, polygonal, and combinations thereof. In some examples, handle 302 may be smooth along its length. In some examples, handle 302 may include indentations and/or protrusions along its length so that a clinician may have a secure grip of handle 302. The indentations and/or protrusions may be located in a pattern along handle 302 or may be arranged in a random pattern. In some examples, handle 302 may have a coating, such as rubber, in order to enhance a clinician's grip of handle 302. In some examples, an outer surface of handle 302 may be textured in order to help provide a secure grip if handle 302 becomes wet or slippery.

In some examples, handle 302 may include a proximal end 304 and a distal end 306. In some examples, distal end 306 may be connected to a dispenser head 308. In one example, handle 302 may include a change, e.g., curves, bends, and angles, along the length of outer surface of handle 302. For example, handle 302 may include curves, bends, angles, along the length of its surface.

In some examples, insertion tool 300 may be made of various materials including metals, metal alloys, plastics and other polymers, composite materials, or any combination thereof. Insertion tool 300 may be made by various manufacturing methods including molding, machining, casting, extruding, and/or combination thereof.

In some examples, handle 302 may be coupled to dispenser head 308. In one example, handle 302 and dispenser head 308 may be one integral piece. In some examples, handle 302 may be coupled to dispenser head 308 in a variety of methods including hinges, adhesives, mechanical interlocks, threaded portions, press fits, friction fits, interference fits, slide fits and/or combinations thereof. In some examples, dispenser head 308 may include a variety of shapes and sizes. In some examples, dispenser head 308 may include a combination of shapes as shown in FIG. 9. Some example shapes include rectangular, circular, oval, various polygonal shapes, and/or complex shapes including combinations thereof.

In some examples, an angle may be defined between the center axis of handle 302 and the center axis of dispenser head 308. FIG. 9 shows the angle as approximately 45 degrees, but the range may be between about 0 to about 180 degrees. In some examples, an angle between handle 302 and dispenser head 308 may be based on ergonomic factors for the clinician.

Figure 10:
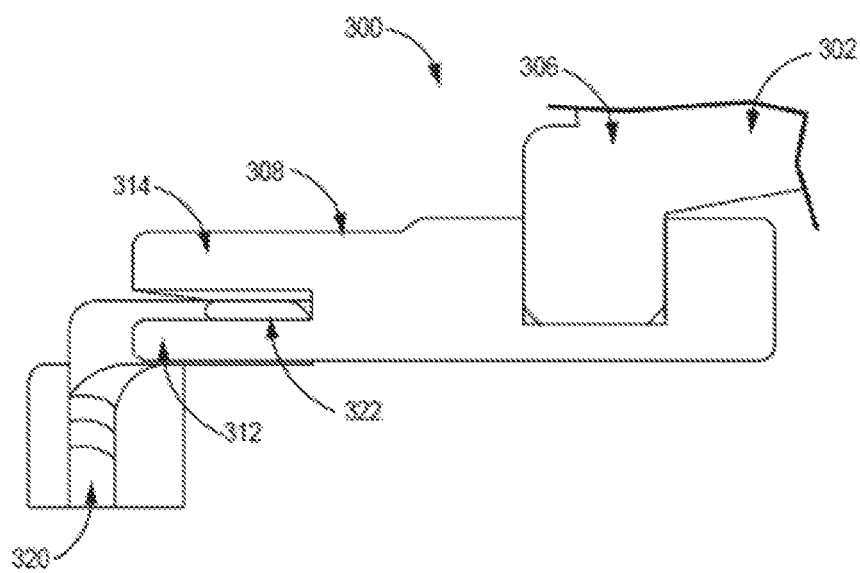
FIG. 10 is a conceptual diagram illustrating a cross-sectional view of a distal end of an insertion tool and an example cranial implant.

In one example, dispenser head 308 may include two prongs 310A and 310B and two tabs 312 and 314 (shown in FIG. 10). In some examples, prongs 310A and 310B may provide visual alignment between dispenser head 308 and cranial implant 320 for capturing and/or recapturing cranial implant 320 for removal from burr hole 24.

FIG. 10 is a cross-sectional view of insertion tool 300 for delivering a cranial implant, in accordance with some examples of this disclosure. Lower tab 312 and upper tab 314 on dispenser head 308 may engage and hold flange 322 (similar to flanges 58 of cranial implant 12) of cranial implant 320, thereby enabling insertion tool 300 to mate with cranial implant 320 for implantation to and/or removal from burr hole 24 before or after lead 14 is delivered to the target site. Flange 322 of cranial implant 320 may be removably inserted into the space defined by lower tab 312 and upper tab 314. Lower tab 312 and upper tab 314 on insertion tool 300 may engage and hold cranial implant 320, allowing installation into and removal from burr hole 24 before or after lead 14 placement.

Figure 11:
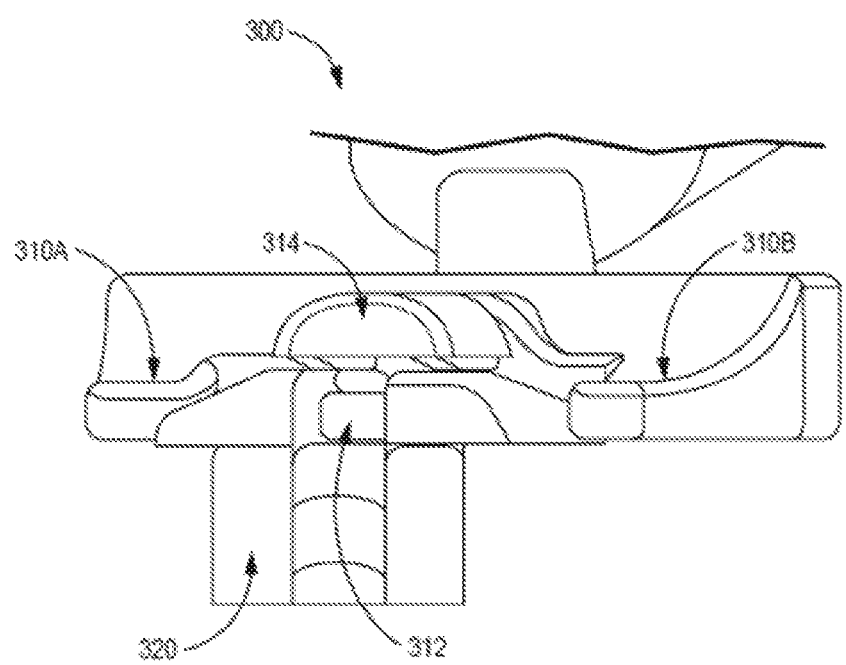
FIG. 11 is a perspective view of an example insertion tool for delivering a cranial implant, in accordance with one or more aspects of this disclosure.

FIG. 11 is a conceptual diagram illustrating a front view of insertion tool 300 for delivering cranial implant 320, in accordance with some examples of this disclosure. By disposing cranial implant 320 between prongs 310A and 310B, a clinician may use prongs 310A and 310B as a proxy for the location of cranial implant 320. Consequently, in some examples, a clinician may deliver cranial implant 320 to its target sire without ever needing to directly visualize cranial implant 320. In one example, insertion tool 300 may remove the necessity of a clinician trying to deliver cranial implant 320 by hand to its delivery site, e.g. burr hole 24. By eliminating the need for a clinician to hand deliver cranial implant 320, surgery procedures may be quicker, more hygienic, and/or less traumatic physically for patient 20.

Figure 12:
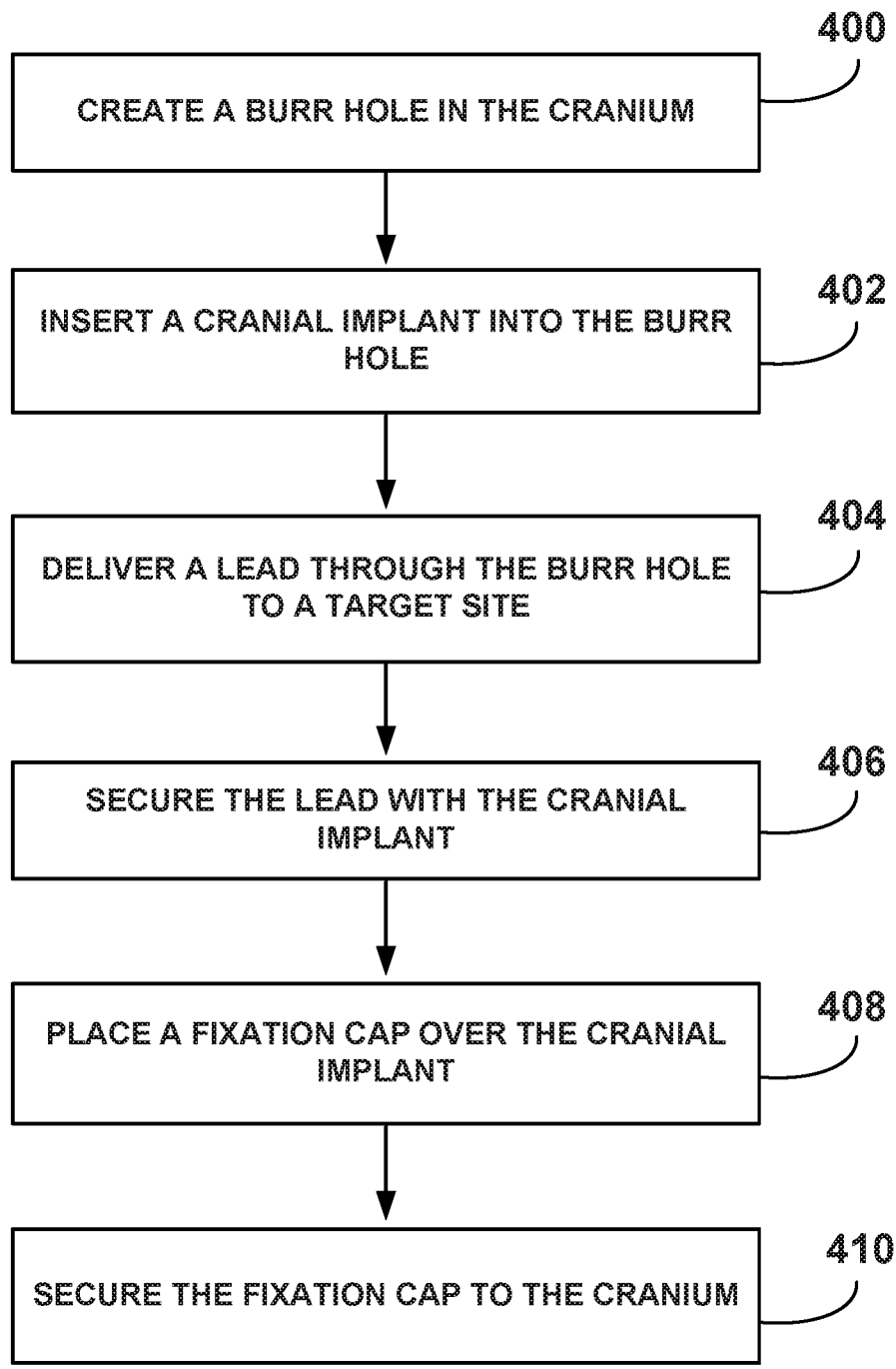
FIG. 12 is a flow diagram illustrating an example process of implanting a cranial implant system to secure an elongated member, in accordance with one or more aspects of this disclosure.

FIG. 12 is a flow diagram illustrating an example process of delivering a cranial implant system, in accordance with one or more aspects of this disclosure. The technique of FIG. 12 will be described with concurrent reference to system 10 of FIG. 1, although a person having ordinary skill in the art will understand that the technique may be performed by another system, and that system 10 may perform other techniques.

A clinician may create burr hole 24 in cranium 22 (400). In some examples, a clinician may make more than one burr hole 24. Although a single lead may be inserted into a single burr hole, multiple leads 14 may be inserted through more than one burr hole 24 in other examples. A frame may be set up on the cranium 22 of patient 20 to help stabilize a twist drill that the clinician may use to remove bone and create burr hole 24.

As described above, once burr hole 24 is created (400), a clinician may insert cranial implant 12 into burr hole 24 (402). Cranial implant 12 of varying sizes and diameters may be used in burr holes 24 made from varying drill diameters from small twist drills (from about 2 mm to about 6 mm) and up to perforator diameters (about 13 mm to about 14 mm). As described above, cranial implant 12 may use an interference fit on the outside surface of cranial implant 12. The interference fit of cranial implant 12 may ensure cranial implant 12 stays secure in burr hole 24. In some examples, bone cement may be filled in burr hole 24 to retain cranial implant 12 in burr hole 24. In some examples, an attachment mechanism (not shown) may be used to connect with a portion of cranial implant 12 to secure cranial implant 12 to the cranium 22 of patient 20. In one example, the attachment mechanism may be bone screws, suturing directly to the surrounding tissue, suturing to mechanical components (e.g., anchors) that are secured (screwed) into cranium 22, securing with various types of straps (e.g., nonmetallic straps) that are screwed down, or the like. For example, an attachment mechanism may be one or more bone screws inserted through a portion of cranial implant 12 and secured to an exterior of cranium 22 of patient 20. In some examples, bone screws may provide cranial implant 12 permanent attachment to cranium 22.

Once cranial implant 12 is secured in burr hole 24, a clinician may deliver lead 14 through burr hole 24 to a target site within cranium 22 of patient 20 (404). In order for lead 14 to reach the target site, a clinician may create a delivery path through the brain of patient 20 to the target site. The clinician may complete a preprocedural magnetic resonance imaging (MRI) scan or use software to create a three-dimensional delivery path. By creating a preprocedural delivery path, the clinician may avoid potential problems, e.g., blood vessels, along the delivery path.

Once lead 14 is delivered to the target site, a clinician may secure lead 14 at least partially within cranial implant 12 (406). Cranial implant 12 may retain lead 14 with at least one flange 58. Lead 14 may be bent towards exterior guide portion 50 and pressed into flange 58 to secure lead 14. Flange 58 of cranial implant 12 may be made of a rigid material to ensure lead 14 may be secure over a long period of time. For example, lead 14 may be secured by flange 58 on the order of years.

In some examples, a technique for inserting cranial implant 12 and securing lead 14 may include other, optional steps in addition to those shown in FIG. 12. For example, the technique of FIG. 12 may optionally include a clinician making incision 26 through the scalp of patient 20 and pulling back a resulting flap of skin to expose the desired area of cranium 22, as described above, before creating burr hole 24 in cranium 22 (400). In some examples, the clinician may make several incisions, e.g., a clinician may make a separate incision for burr hole 24, lead 14, and IMD 16. In some examples, incision 26 may be any shape, including a straight line, an uneven line, a geometric shape, or any combination thereof. Incision 26 may, as shown in FIG. 2, be generally shaped like a "C."

In some examples, the steps of technique of FIG. 12 may be rearranged. For example, the step of inserting cranial implant 12 into burr hole 24 (402) may come after delivering lead 14 through burr hole 24 to a target site (404). In some examples, before inserting a cranial implant 12 into burr hole 24 (402), a clinician may secure lead 14 with cranial implant 12 (406) before delivering lead 14 through burr hole 24 to a target site (404). The provided examples of rearranging the steps are nonlimiting and other steps may be rearranged, added, or removed when developing a technique to insert cranial implant 12 and/or deliver lead 14.

In some examples, the technique of FIG. 12 may optionally include placing fixation plate 100 adjacent cranial implant 12 or placing fixation cap 200 (or any other fixation member, e.g., fixation cap 220) over cranial implant 12 (408). In some examples, bone cement may be used to secure the fixation plate 100 or the fixation cap 200 to cranium 22. In some examples, one or more bone screws may be used to secure fixation plate 100 or fixation cap 200 to cranium 22. In one example, a combination of bone cement and one or more bone screws may be used to secure fixation plate 100 or fixation cap 200 to cranium 22. In other examples, the method of implanting the elongated member of lead 14 may include wrapping the lead around fixation cap 200 to secure excess length of lead 14.

Figure 13:
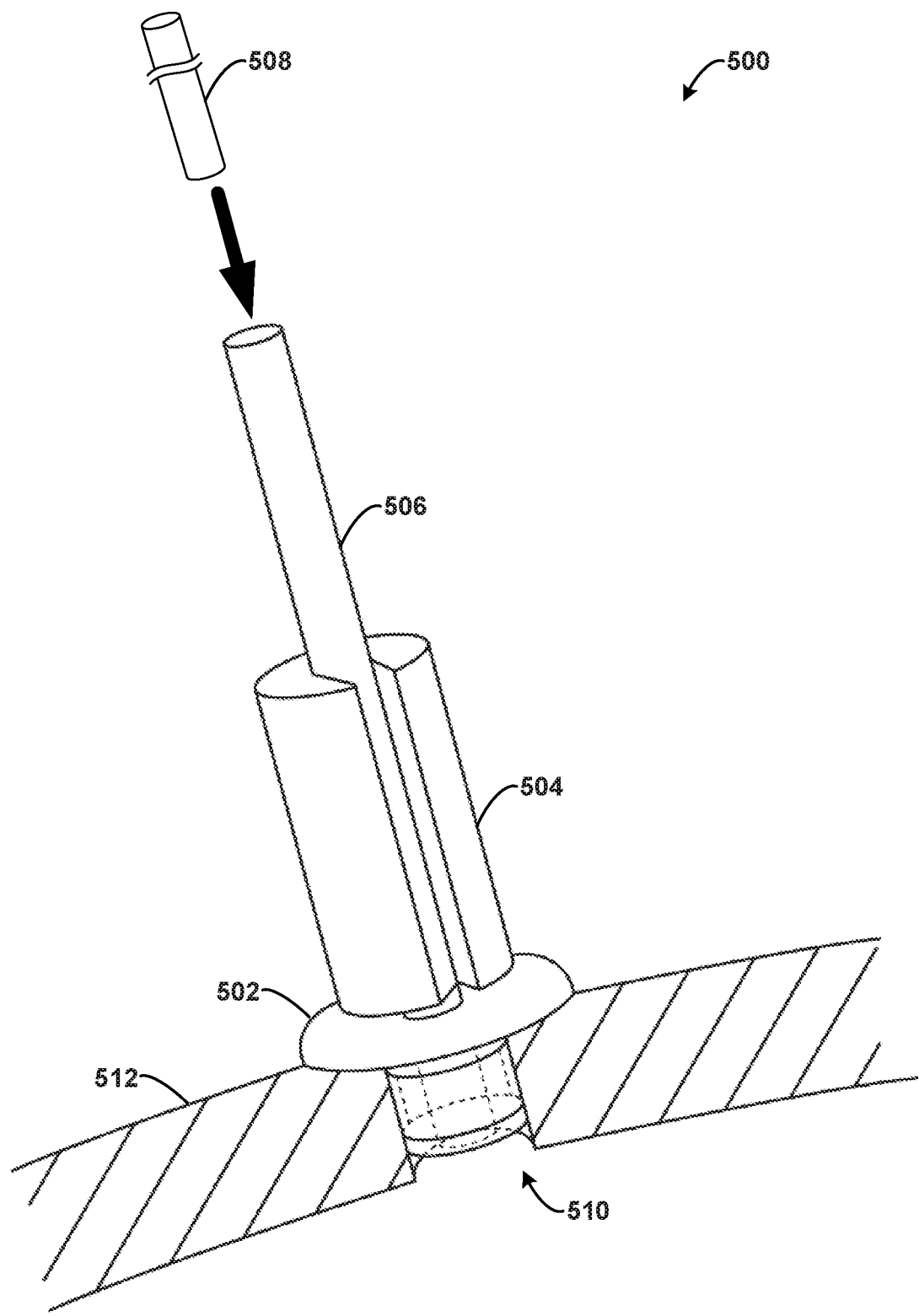
FIG. 13 is a conceptual diagram illustrating an example cranial implant system, in accordance with one or more aspects of this disclosure.

FIG. 13 is a conceptual diagram illustrating an example cranial implant system 500, in accordance with one or more aspects of this disclosure. Cranial implant system 500 includes a cranial implant 502, a plug retainer 504, a cannula 506, and/or an elongated member 508. In some examples, elongated member 508 may be a lead (e.g., a lead carrying one or more electrodes) or a catheter (e.g., a drug delivery catheter). Cranial implant system 500 may be used by a clinician to insert cranial implant 502 into a burr hole 510 of a cranium 512. Plug retainer 504 can serve multiple purposes. For example, plug retainer 504 can be used to help apply force in the direction of cranium 512 and to cranial implant 502 to facilitate insertion of cranial implant 502 in burr hole 510. When removing cannula 506 from cranial implant 502 and burr hole 510, the clinician can hold plug retainer 504 against cranial implant 502 in order maintain cranial implant 502 in burr hole 510.

The interference fit (e.g., the bias or frictional force) between cranium 512 and the exterior surface of cranial implant 502 may vary due to a number of factors, such as exact diameter of the burr hole, patient-specific thickness of cranium 512, expected forces acting on the burr hold during patient movement, or other patient-specific criteria. As a result, portions of cranium 512 may benefit from different friction forces between cranial implant 502 and cranium 512. Plug retainer 504 may provide the clinician with a surface to grab with the hand or fingers to apply the force against cranial implant 502 that enables insertion of cranial implant 502 into burr hole 510. Cranial implant 502 may be constructed from similar material(s) and/or have similar dimensions as cranial implant 12. In some examples, cranial implant 502 may be configured to be inserted into burr hole 510 without the use of plug retainer 504 or cannula 506. For example, cranial implant 502 can be manually pressed into burr hole 510 using fingers of the clinician or using a specialized surgical or delivery tool (e.g., forceps).

Plug retainer 504 or cannula 506 may be constructed of one or more polymers, composite materials, metal alloys, or other material. In some examples, cannula 506 may include a rigid wall that resists compression from external forces to enable relatively easy insertion of lead 508 through cannula 506 and the channel within cranial implant 502.

Figure 14:
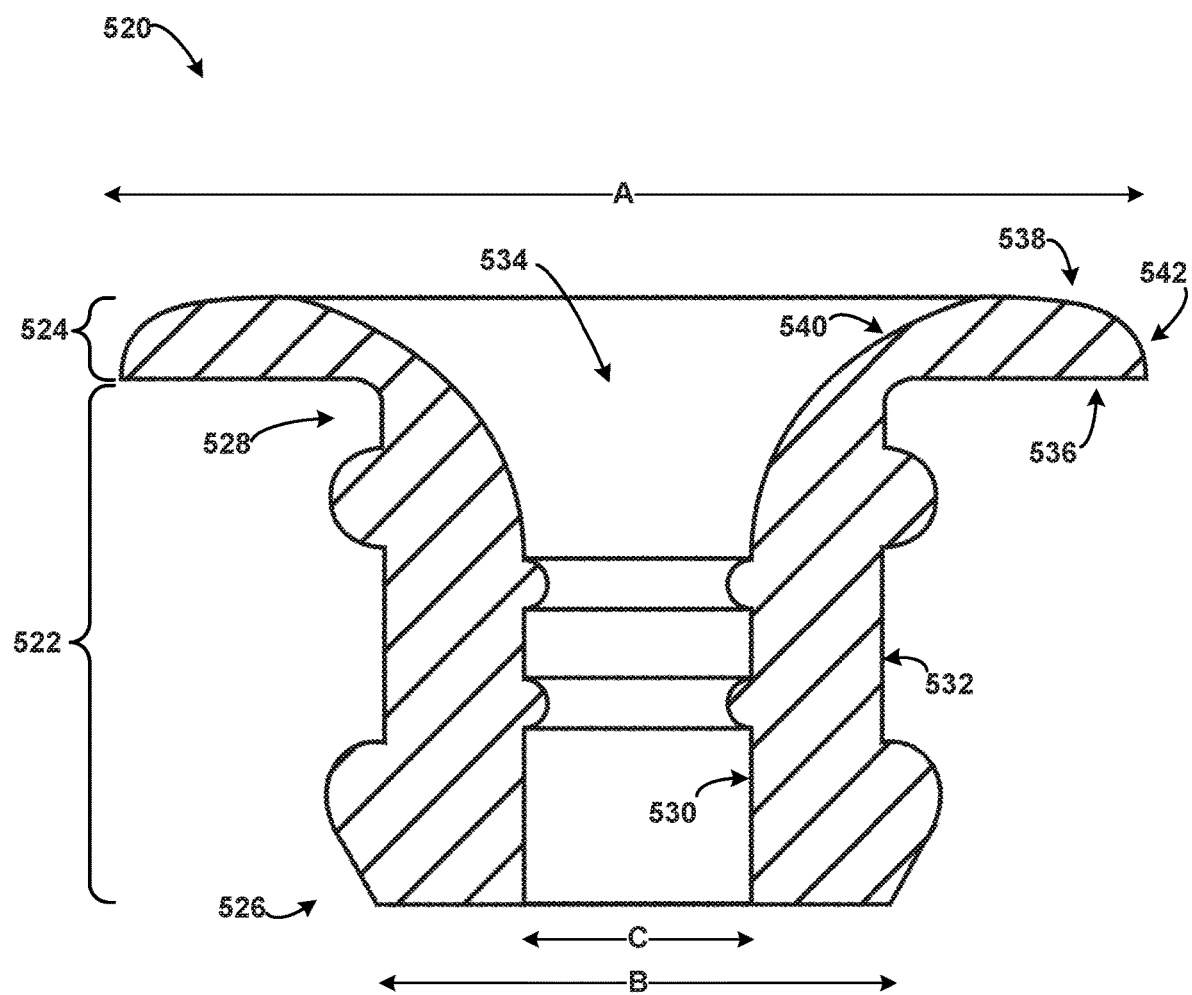
FIG. 14 is a perspective view of an example cranial implant, in accordance with one or more aspects of this disclosure.

FIG. 14 is a perspective view of an example cranial implant 520, in accordance with one or more aspects of this disclosure. Cranial implant 520 may be the same or substantially similar to cranial implant 502. In some examples, a cranial implant 520 may be constructed from similar material and have similar dimensions as cranial implants 12 and 502. For example, cranial implant 520 can be constructed of at least one of silicone, polyurethane, or low-density polyethylene (LDPE).

Cranial implant 520 includes an interior guide portion 522 and an exterior guide portion 524. Interior guide portion 522 is configured to be disposed in a burr hole of a cranium. Interior guide portion 522 includes a first distal end 526, a first proximal end 528, a first inner surface 530, and a first outer surface 532. First distal end 526 is configured to be inserted further into the burr hole than first proximal end 528. First inner surface 530 at least partially defines a channel 534 configured to accept an elongated member, such as a lead or catheter. Exterior guide portion 524 extends from interior guide portion 522 and is configured to contact an external surface of the cranium. Exterior guide portion 524 includes a second distal end 536, a second proximal end 538, a second inner surface 540, and a second outer surface 542. Second inner surface 540 at least partially defines channel 534 extending from interior guide portion 522. A second diameter ("A" in FIG. 14) of second outer surface 542 of exterior guide portion 524 is larger than a first diameter ("B" in FIG. 14) of first outer surface 532 of interior guide portion 522.

In some examples, an inner diameter ("C" in FIG. 14) of interior guide portion 522 can be greater than an outer diameter of a cannula (e.g., cannula 506 of FIG. 13), and an outer diameter ("B" in FIG. 14) of interior guide portion 522 can be configured to be greater than a diameter of the burr hole (e.g., burr hole 510 of FIG. 13) in order to provide a friction fit between cranial implant 520 retention in the burr hole. In some examples, burr hole 510 may have a diameter selected from approximately 3 mm to approximately 6 mm.

In some examples, cranial implant 520 can be part of a system further including other components, e.g., a fixation cap, a fixation plate, and/or a bone screw. In some examples, a fixation cap can contact the cranium. Cranial implant 520 can stabilize the elongated member in the burr hole. The fixation cap can securely anchor an elongated member for chronic retention. The fixation cap can define a recess that accepts exterior guide portion 524, and the fixation cap can define a second channel configured to accept a portion of the elongated member, such as a lead, extending out from channel 534, and defining a curved track. The curved track can be configured to facilitate the elongated member being wrapped within the curved track and around the fixation cap. The bone screw can be configured to secure the fixation cap to the cranium. In some examples, a fixation plate can be configured to contact the cranium and secure the elongated member on the external surface of the cranium.

Figure 15A:
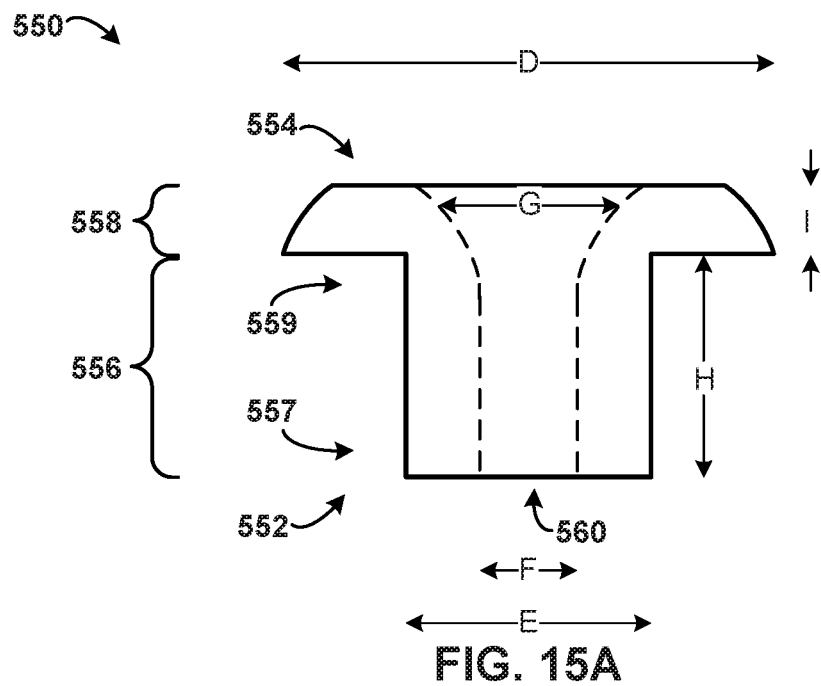
FIG. 15A is a side view of an example cranial implant, in accordance with one or more aspects of this disclosure.
Figure 15B:
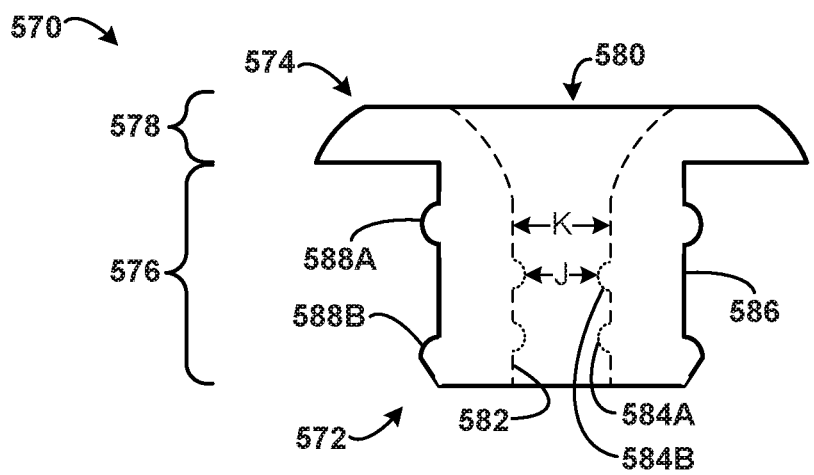
FIG. 15B is a side view of an example cranial implant, in accordance with one or more aspects of this disclosure.
Figure 15C:
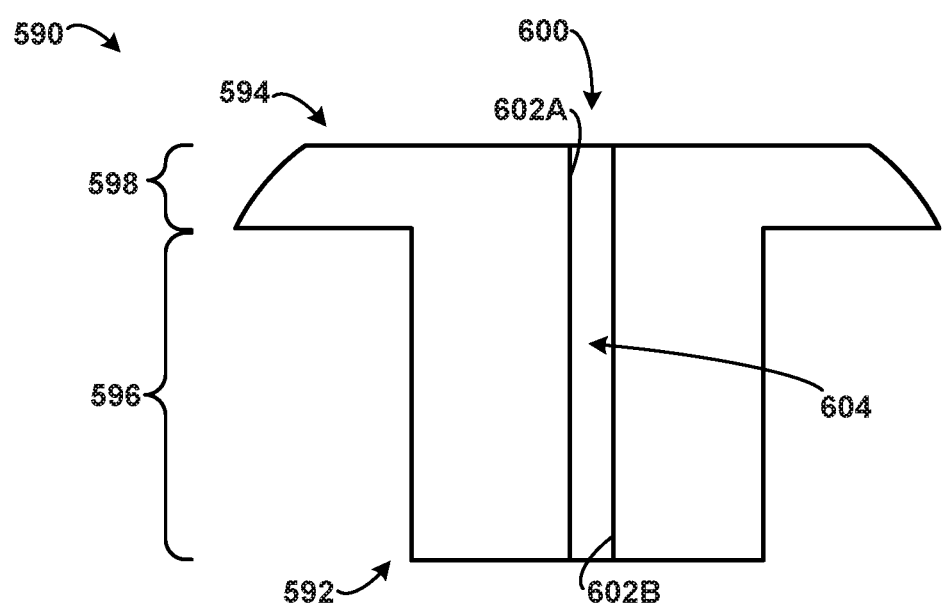
FIG. 15C is a side view of an example cranial implant, in accordance with one or more aspects of this disclosure.

FIGS. 15A, 15B, and 15C are side perspective views of example cranial implants, in accordance with one or more aspects of this disclosure. FIG. 15A shows an example cranial implant 550 with a distal end 552, a proximal end 554, an interior guide portion 556 with a distal end 557 and a proximal end 559, an exterior guide portion 558, and a channel 560 extending between distal end 552 and proximal end 554 and extending through both of interior guide portion 556 and exterior guide portion 558. In some examples, an inner diameter "F" of interior guide portion 556 may be selected from approximately 0.762 millimeters (mm) (0.030 inches (in)) to approximately 2.032 mm (0.080 in), an outer diameter "E" range of interior guide portion 556 may be selected from approximately 1.778 mm (0.070 in) to approximately 15.240 mm (0.600 in), and extend into the skull a depth "H" selected to be from approximately 1.016 mm (0.040 in) to approximately 7.620 mm (0.300 in). In some examples, an inner diameter "G" of exterior guide portion 558 may be selected from approximately 0.762 millimeters (mm) (0.030 inches (in)) to approximately 15.240 mm (0.600 in), an outer diameter "D" range of exterior guide portion 558 may be selected from approximately 1.778 mm (0.070 in) to approximately 15.240 mm (0.600 in), and a height "I" of exterior guide portion 558 may be selected from approximately 0.762 mm (0.030 in) to approximately 2.540 mm (0.100 in). In some examples, an inner diameter "F" of channel 560 may gradually increase moving in a proximal direction along a length of cranial implant 550 from the distal end 552 of interior guide portion 556 to proximal end 554.

FIG. 15B shows an example cranial implant 570 (which may be similar to cranial implant 502) with a distal end 572, a proximal end 574, an interior guide portion 576, an exterior guide portion 578, and a channel 580 extending between distal end 572 and proximal end 574 and extending between interior guide portion 576 and exterior guide portion 578. Interior guide portion 576 includes a first inner surface 582 and a first outer surface 586. In some examples, cranial implant 570 includes at least one surface feature 588 (e.g., surface features 588A and 588B, collectively "surface features 588") disposed on first outer surface 586 of interior guide portion 576. Surface features 588 are configured to contact an inner surface of the burr hole to provide a friction fit that retains interior guide portion 576 within the burr hole.

Surface features 588 can include at least one of a bump, rib, roughened or textured surface, wipers (e.g., one or more flaps extending perpendicular and/or orthogonal to first inner surface 582) or any other such features. Surface features 588 may deform when cranial implant 570 is inserted into the burr hole such that the deformation provides a bias against the burr hole wall. In some examples, surface features 588 may be separate or integral and may be made of the same material as interior guide portion 576. In some examples, surface features 588 can be constructed of silicone, metal, plastic, or ceramic. In some examples, surface features 588 can be shaped, e.g., slopping radially outward and proximally, in order to ease insertion of cranial implant 570 into the burr hole and resist removal of cranial implant 570 from the burr hole. In some examples, other than surface features 588 configured to retain cranial implant 570 in the burr hole, an adhesive, such as bone cement, can be disposed on first outer surface 586 of interior guide portion 576.

In some examples, surface features 584 (i.e., surface features 584A and 584B, collectively "surface features 584") can be disposed on first inner surface 582 of interior guide portion 576, and surface features 584 can contact the elongated member, such as a lead, to retain the elongated member at least partially within channel 580. In some examples, surface features 584 on first inner surface 582 defines a retention diameter "J" that is smaller than a channel diameter "K" defined by first inner surface 582.

FIG. 15C shows an example cranial implant 590 which may be similar to cranial implant 12 or 502. Cranial implant 590 includes a distal end 592, a proximal end 594, an interior guide portion 596, an exterior guide portion 598, and a channel 600 (similar to channel 560 of FIG. 15A) extending from distal end 592 to proximal end 594 and extending through interior guide portion 596 and exterior guide portion 598.

Cranial implant 590 defines a first edge 602A and a second edge 602B (collectively "pair of edges 602") extending the entire length of cranial implant 590 such that pair of edges 602 define a longitudinal slot 604 along the length of cranial implant 590 and through interior guide portion 596 and exterior guide portion 598. In some examples, longitudinal slot 604 may enable cranial implant 590 to increase or decrease the circumference of interior guide portion 596 to fit a range of burr hole sizes. Longitudinal slot 604 may also decrease the force needed to insert cranial implant 590 into the burr hole because interior guide portion 596 may reduce in circumference.

Figure 16:
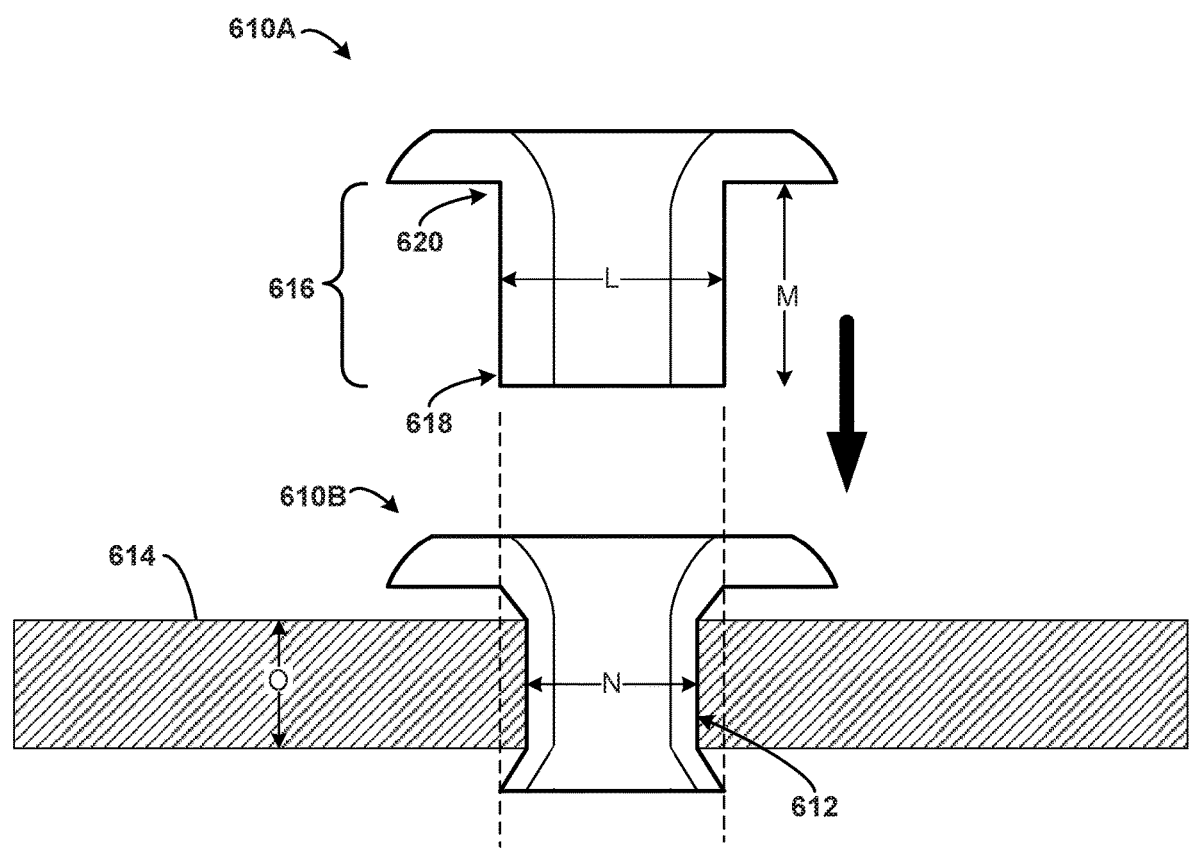
FIG. 16 is a cross-sectional view of an example cranial implant.

FIG. 16 is a cross-sectional view of an example cranial implant 610. Cranial implant 610 may be similar to cranial implant 502, for example. Cranial implant 610 (cranial implant 610 is shown in the pre-insertion configuration of 610A and post-insertion configuration of 610B) includes a distal end 618 and a proximal end 620 and is shown in configuration 601A outside of burr hole 612 of a cranium 614.

Cranial implant 610 can be constructed of a flexible material configured to be compressible in order for the interior portion to be pressed into burr hole 612. An outer diameter "L" of an interior guide portion 616 can be greater than a diameter "N" of burr hole 612, a length "M" of interior guide portion 616 can be greater than a depth "O" of burr hole 612 and cranium 614. The middle of interior guide portion 616 is configured to be compressed radially inwards when inserted into burr hole 612 which can provide a bias against the wall of burr hole 612. In addition, distal end 618 of interior guide portion 616 can extend distally out from burr hole 612 and radially outward from diameter "N" of burr hole 612. This "flare" outwards in distal end 618 in cranial implant 610 can help retain cranial implant 610 in burr hole 612. In some examples, the outer diameter "L" of interior guide portion 616 at the distal end 618 may be ramped or sloped to a smaller distal diameter to facilitate insertion of distal end 618 into burr hole 612.

In some examples, outer diameter "L" of interior guide portion 616 can be selected from about 3 millimeters (mm) to about 8 mm, which may be selected to correspond to certain diameters "B" of burr hole 612 which may range from about 2 millimeters (mm) to about 7 mm. In some examples, the uncompressed diameter of configuration 610A of cranial implant 610 may be selected to be approximately 0.5 mm to approximately 4.0 mm larger than the diameter "N" of burr hole 612.

Figure 17:
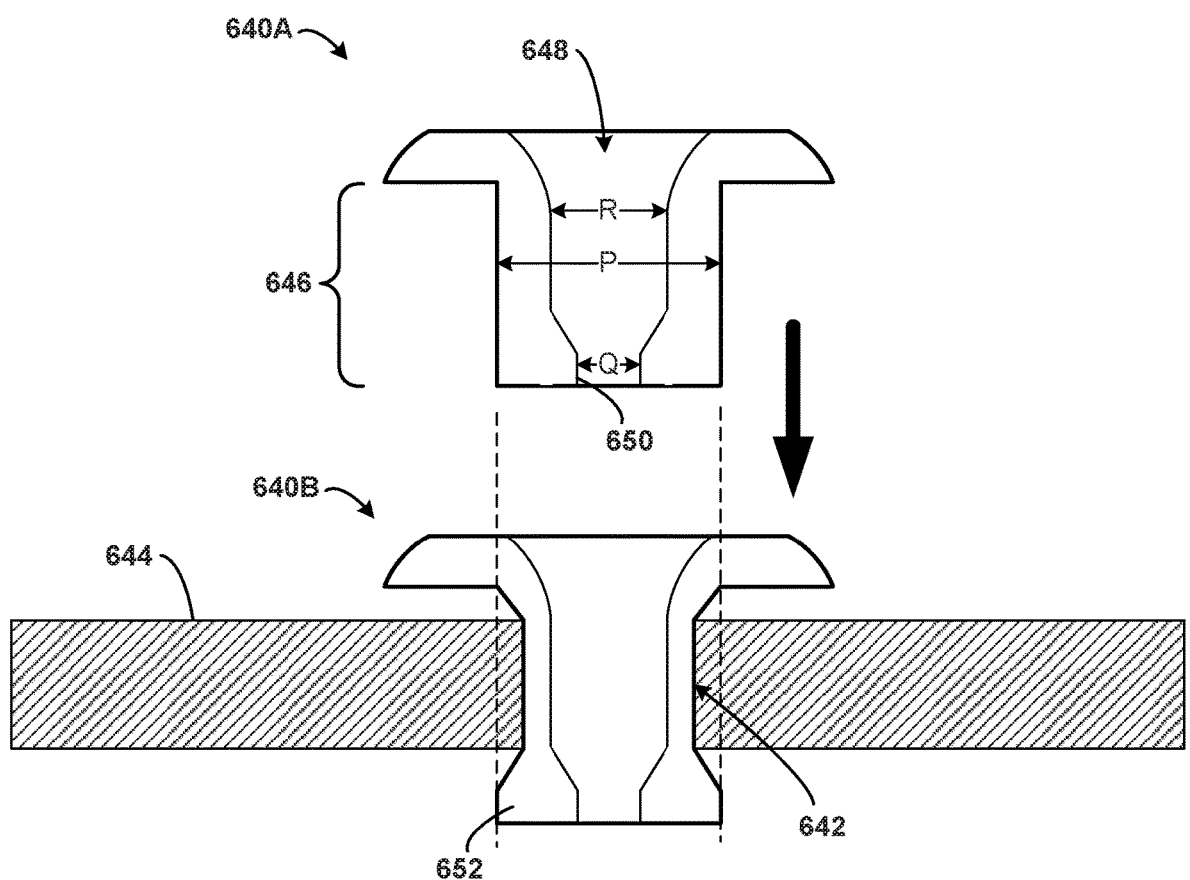
FIG. 17 is a cross-sectional view of an example cranial implant.

FIG. 17 is a cross-sectional view of an example cranial implant 640, which may be similar to cranial implant 502 or 610. Cranial implant 640 (cranial implant 640 is shown the pre-insertion configuration 640A and the post-insertion configuration 640B) can is configured to be inserted into a burr hole 642 of a cranium 644. The diameter "R" of channel 648 can be selected to be greater than an outer diameter of the elongated member, e.g., a cannula, to be inserted within interior guide portion 646. The difference in diameter "A" from the outer diameter of the elongated member can provide clearance to facilitate insertion of the elongated member into cranial implant 640. The outer diameter "P" of interior guide portion 646 can be configured to retain cranial implant 640 in burr hole 642. In some examples, at least one surface feature 650 of channel 648 can provide a reduced-diameter section of channel 648. The diameter "Q" of the reduced-diameter section of channel 648 can be selected to be less than an outer diameter of an elongated member, such as a lead, that, when the at least one surface feature 650 is compressed against the inserted elongated member, provides an interference fit that retains the elongated member within cranial implant 640. In some examples, cranial implant 640 can be configured to be flexible in order to be compressed within burr hole 642 such that confirmation 640B includes a flared outward portion 652 of cranial implant 640 at the distal end of cranial implant 640 when interior guide portion is inserted fully into burr hole 642.

Figure 18A:
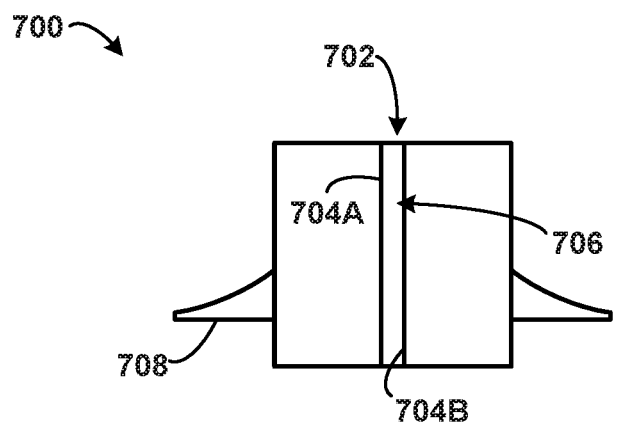
FIG. 18A is a side view of an example plug retainer, in accordance with one or more aspects of this disclosure.
Figure 18B:
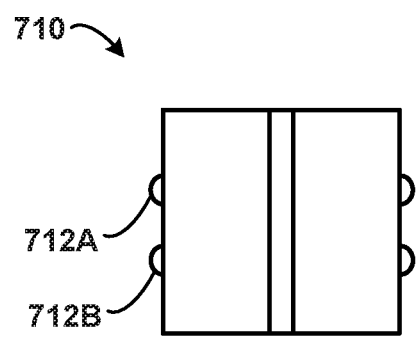
FIG. 18B is a side view of an example plug retainer, in accordance with one or more aspects of this disclosure.

FIGS. 18A and 18B are side views of example plug retainers, in accordance with one or more aspects of this disclosure. Plug retainers 700 and 710 may be similar to plug retainer 504 of FIG. 14. As shown in the example of FIG. 18A, a channel 702 of plug retainer 700 can be configured to accept an elongated member, such as a cannula or an elongated member. Plug retainer 700 defines a first edge 704A and a second edge 704B (collectively "edges 704") extending the length of plug retainer 700 such that pair of edges 704 define a longitudinal slot 706 along the length of plug retainer 700. Longitudinal slot 706 may be configured to accept an elongated member or cannula into channel 702 and/or remove plug retainer 700 from the elongated member or cannula. In some examples, a surface feature 708, such as a curved flange or handle, can be disposed on an outer surface of plug retainer 700 to enable a clinician to grip and apply a force to plug retainer 700. Surface feature 708 may include one or more separate structures positioned at various positions around the perimeter of plug retainer 700. In other examples, surface feature 708 may completely encircle the perimeter of plug retainer 700 which may, or may not, extend beyond one or both of edges 704.

As shown in FIG. 18B, plug retainer 710 may be similar to plug retainer 504 of FIG. 14 or plug retainer 700 of FIG. 18A. Plug retainer 710 can include one or more surface features such as one or more ribs 712A and 712B. Ribs may be similar to detents which are positioned at a partial perimeter position or extending partially or fully around the perimeter of plug retainer 710. In other examples such as ribs. Surface features 708 may include, instead of or in addition to ribs 712A and 712B, one or more wings, fins, ribs, bumps, contours, or textured surfaces that facilitate friction for handling by a clinician.

Figure 19:
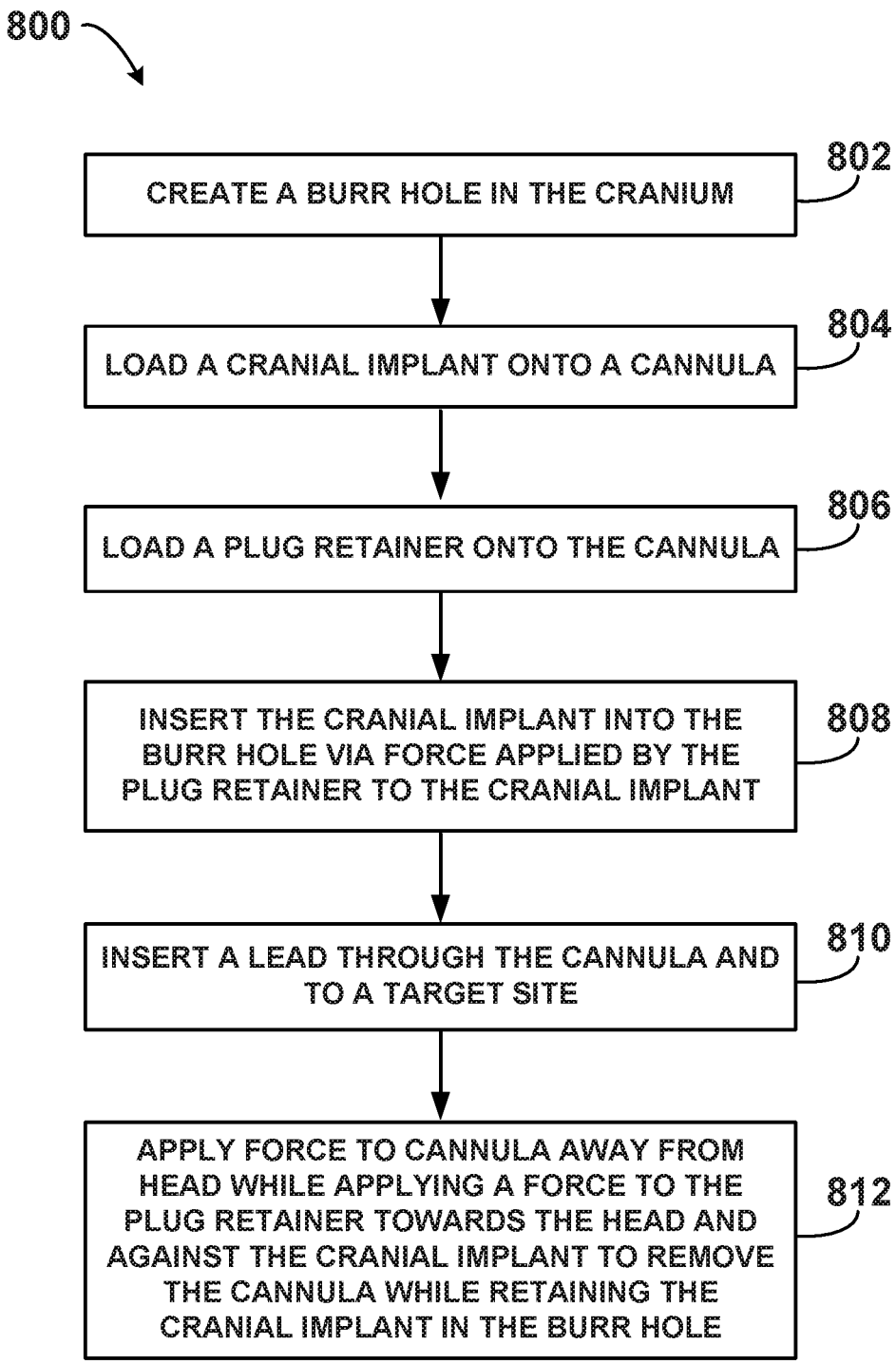
FIG. 19 is a flow diagram illustrating an example process of implanting a cranial implant system to secure an elongated member, in accordance with one or more aspects of this disclosure.

FIG. 19 is a flow diagram illustrating an example process 800 of implanting a cranial implant, such as cranial implant 502, from system 500 to secure an elongated member, in accordance with one or more aspects of this disclosure. The technique of FIG. 19 will be described with concurrent reference to cranial implant 502 and system 500 of FIG. 13, this technique may be applicable to other cranial implants, such as those described herein, which are configured to be implanted within a burr hole or other opening in a cranium.

As shown in the example of FIG. 19, a clinician may create burr hole 510 in cranium 512 (800). For example, the clinician may use a bone drill to create burr hole 510. Although a single lead may be inserted into a single burr hole, multiple leads may be inserted through more than one burr hole 510 in other examples. In some examples, a frame may be set up on the cranium 512 of patient to help stabilize a twist drill that the clinician may use to remove bone and create burr hole 510. Cranial implant 502 of varying sizes and diameters may be used in burr holes 510 made from varying burr hole diameters created by small twist drills (from about 2 mm to about 6 mm) and up to perforator diameters (about 13 mm to about 14 mm) in other examples The clinician may load cranial implant 502 onto cannula 506 (804). In addition, the clinician may load plug retainer 504 onto cannula 506 (806). In some examples, cranial implant 502 and/or plug retainer may be pre-loaded on cannula 506 after plug retainer 504. In some examples, plug retainer 504 may not be used to deliver cranial implant 502, and cranial implant 502 may be delivered without being loaded onto cannula 506 first. In other examples, cranial implant 502 and/or plug retainer may be pre-loaded on cannula 506 by the manufacturer and ready to be implanted straight from the package.

After cranial implant 502 and plug retainer 504 are loaded onto cannula 506, the clinician may insert cranial implant 502 into burr hole 510 with the help of plug retainer 504 (808). As described above, cranial implant 502 may provide an interference fit between the outside surface of cranial implant 502 and the interior wall of the burr hole. The interference fit of cranial implant 502 may ensure cranial implant 502 stays secure in burr hole 510. In some examples, bone cement may be filled in burr hole 510 or on the outside of cranial implant 502 to retain cranial implant 502 in burr hole 510. Once cannula 506 and cranial implant 502 are inserted in burr hole 510, the clinician may insert elongated member 508 through cannula 506 and to a target site (810). In other examples, elongated member 508 may be pre-loaded into cannula 506.

After elongated member 508 is implanted, cannula 506 can be removed from burr hole 510 while retaining cranial implant 502 in burr hole 510 with plug retainer. For example, the clinician can apply a force to cannular 506 in a direction away from the head of the patient while applying a force to plug retainer 504 towards the head and against cranial implant 502 to remove cannula 506 while retaining cranial implant 502 within burr hole 510 (812). In other examples, the clinician may first remove, with plug retainer 504, cannula 506 from cranial implant 502 and then insert elongated member 508 through cranial implant 502 to a target site.

In some examples, if there is an excess length of elongated member 508, extending out from cranial implant 502, a clinician may wind the excess length of elongated member 508 around a track disposed on an underside of a fixation cap that is later placed over cranial implant 502. The clinician may then secure the fixation cap to cranium 512 which also secures the elongated member 508 to the cranium. As discussed herein, the elongated member may be a lead carrying one or more electrodes and/or a catheter defining a lumen configured to deliver a fluid to, or remove fluid from, the interior of the cranium.

The following examples are described herein. Example 1: A cranial implant comprising: an arcuate guide portion configured to be disposed in a burr hole of a cranium, the arcuate guide portion comprising a distal end, a proximal end, an inner surface, and an outer surface, the distal end configured to be inserted further into the burr hole than the proximal end, and the inner surface configured to at least partially define a first channel that accepts an elongated member, wherein the outer surface extends around less than a full circumference of the burr hole; an exterior guide portion coupled to the arcuate guide portion and configured to contact an external surface of the cranium, the exterior guide portion defining a second channel configured to accept the elongated member; and one or more flanges coupled to the exterior guide portion and configured to retain the elongated member at least partially within the second channel.

Example 2: The cranial implant of example 1, wherein the first channel defines a center axis, and wherein the exterior guide portion extends radially outward from the center axis, the exterior guide portion configured to extend over less than the full circumference of the burr hole.

Example 3: The cranial implant of example 1 or 2, wherein a distal cranially facing surface of the exterior guide portion is configured to couple to the proximal end of the arcuate guide portion and extend over the burr hole, and wherein a proximal cranially facing surface of the exterior guide portion is configured to contact the external surface of the cranium away from the burr hole.

Example 4: The cranial implant of any one of examples 1 to 3, wherein a center axis of the first channel is substantially orthogonal to a center axis of the second channel.

Example 5: The cranial implant of any one of examples 1 to 4, wherein the exterior guide portion comprises two wing segments coupled to the arcuate guide portion, and wherein opposing surfaces of the two wing segments at least partially define the second channel.

Example 6: The cranial implant of example 5, wherein each wing segment of the two wing segments comprises an inner edge defining a portion of the second channel and an outer edge opposing the inner edge, and wherein, for each of the two wing segments, a respective flange of the one or more flanges extends from the inner edge of the respective wing segment to at least partially define the second channel.

Example 7: The cranial implant of example 6, wherein the one or more flanges and the inner edge of the arcuate guide together form a substantially continuous surface.

Example 8: The cranial implant of any one of examples 5 to 7, wherein the two wing segments extend radially outward from the proximal end of the arcuate guide portion.

Example 9: The cranial implant of any one of examples 1 to 8, wherein the outer surface of the arcuate guide portion faces a radially outward direction and is substantially coaxial with the inner surface of the arcuate guide.

Example 10: The cranial implant of any one of examples 1 to 9, further comprising a fixation plate configured to contact the cranium and secure the elongated member in the second channel.

Example 11: The cranial implant of any one of examples 1 to 9, further comprising a fixation cap configured to contact the cranium, the fixation cap defining a recess that accepts the exterior guide portion, defining a third channel configured to accept a portion of the elongated member extending out from the second channel, and defining a curved track, wherein the curved track is configured to facilitate the elongated member being wrapped within the curved track and around the fixation cap.

Example 12: The cranial implant of any one of examples 1 to 11, wherein the cranial implant comprises at least one material selected from the group comprising silicone, polyurethane, and low-density polyethylene (LDPE).

Example 13: The cranial implant of any one of examples 1 to 12, wherein the arcuate guide portion comprises a first material and the exterior guide portion comprises a second material different than the first material.

Example 14: The cranial implant of any one of examples 1 to 13, wherein the first channel and the second channel provide a path for the elongated member from the exterior of the cranium and through the burr hole.

Example 15: The cranial implant of any one of examples 1 to 14, wherein the cranial implant is sized and configured to be inserted in the burr hole, wherein the burr hole has a diameter range of between about 2 millimeters (mm) and about 14 mm.

Example 16: A cranial implant system comprising: a cranial implant comprising: an arcuate guide portion configured to be disposed in a burr hole of a cranium, the arcuate guide portion comprising a distal end, a proximal end, an inner surface, and an outer surface, the distal end configured to be inserted further into the burr hole than the proximal end, and the inner surface configured to at least partially define a first channel that accepts an elongated member, wherein the outer surface extends around less than a full circumference of the burr hole; an exterior guide portion coupled to the arcuate guide portion and configured to contact an external surface of the cranium, the exterior guide portion defining a second channel configured to accept the elongated member; and one or more flanges coupled to the exterior guide portion and configured to retain the elongated member at least partially within the second channel; and a fixation cap configured to at least partially cover the cranial implant and define a routing channel for at least a portion of the elongated member.

Example 17: The cranial implant system of example 16, wherein the fixation cap is configured to be secured to the cranium.

Example 18: The cranial implant system of example 16 or 17, further comprising a bone screw configured to secure the fixation cap to the cranium.

Example 19: A method comprising: inserting an elongated member from an exterior of a cranium through a burr hole and to a target site within the cranium; and inserting a cranial implant configured to retain the elongated member with respect to the cranium, the cranial implant comprising: an arcuate guide portion configured to be disposed in the burr hole of the cranium, the arcuate guide portion comprising a distal end, a proximal end, an inner surface, and an outer surface, the distal end configured to be inserted further into the burr hole than the proximal end, and the inner surface configured to at least partially define a first channel that accepts the elongated member, wherein the outer surface extends around less than a full circumference of the burr hole; an exterior guide portion coupled to the arcuate guide portion and configured to contact an external surface of the cranium, the exterior guide portion defining a second channel configured to accept the elongated member; and one or more flanges coupled to the exterior guide portion and configured to retain the elongated member at least partially within the second channel.

Example 20: The method of example 19, further comprising inserting the elongated member past the flanges into the second channel to retain the elongated member.

Example 21: The method of example 19 or 20, further comprising: winding an excess length of the elongated member around a track disposed on an underside of a fixation cap; placing the fixation cap over the cranial implant; and securing the fixation cap to the cranium.

Example 22: A cranial implant comprising: an interior guide portion configured to be disposed in a burr hole of a cranium, the interior guide portion comprising a first distal end, a first proximal end, a first inner surface, and a first outer surface, the distal end configured to be inserted further into the burr hole than the proximal end, and the first inner surface at least partially defines a channel configured to accept an elongated member; and an exterior guide portion extending from the interior guide portion and configured to contact an external surface of the cranium, the exterior guide portion comprising a second distal end, a second proximal end, a second inner surface, and a second outer surface, wherein the second inner surface at least partially defines the channel extending from the interior guide portion, and wherein a second diameter of the second outer surface of the exterior guide portion is larger than a first diameter of the first outer surface of the interior guide portion.

Example 23: The cranial implant of example 22, wherein an inner diameter of the interior guide portion is greater than an outer diameter of a cannula, an outer diameter of the interior guide portion is configured to be greater than a diameter of the burr hole in order to provide cranial implant retention in the burr hole, and an inner diameter of the distal end of the interior guide portion is less than an outer diameter of the elongated member inserted in the cranial implant in order to retain the elongated member in the cranial implant.

Example 24: The cranial implant of example 22 or 23, wherein: the cranial implant is constructed of a flexible material, the outer diameter of the interior guide portion is configured to be greater than a diameter of the burr hole, a length of the interior guide portion is greater than a depth of the burr hole, a middle portion of the interior guide portion is configured to be compressed radially inwards when inserted into the burr hole, and the distal end of the interior guide portion extends distal from the burr hole and radially outward from the diameter of the burr hole when inserted into the burr hole.

Example 25: The cranial implant of any one of examples 22 to 24, wherein an inner diameter of the channel gradually increases moving in a proximal direction along a length of the cranial implant to the first proximal end of the interior guide portion.

Example 26: The cranial implant of any one of examples 22 to 25, wherein the cranial implant is constructed of at least one of silicone, polyurethane, or low-density polyethylene (LDPE).

Example 27: The cranial implant of any one of examples 22 to 26, further comprising at least one surface feature disposed on the first outer surface of the interior guide portion, the at least one surface feature configured to contact an inner surface of the burr hole to retain the interior guide portion within the burr hole.

Example 28: The cranial implant of example 27, wherein the at least one surface feature comprises at least one of a bump, rib, textured surface, or wiper.

Example 29: The cranial implant of example 27, wherein the at least one surface feature is integral with the interior guide portion.

Example 30: The cranial implant of any one of examples 22 to 29, further comprising at least one surface feature disposed on the first inner surface of the interior guide portion, the at least one surface feature configured to contact the elongated member to retain the elongated member at least partially within the channel.

Example 31: The cranial implant of example 30, wherein the at least one surface feature comprises at least one of a bump, rib, textured surface, or wiper.

Example 32: The cranial implant of any one of examples 22 to 31, wherein an outer diameter of the interior guide portion extends from about 3 millimeters (mm) to about 8 mm, and wherein the burr hole has a diameter range extends from about 2 millimeters (mm) to about 7 mm.

Example 33: The cranial implant of any one of examples 22 to 32, wherein an outer diameter of the interior guide portion extends from about 3 millimeters (mm) to about 8 mm and the cranial implant is configured to be inserted in the burr hole.

Example 34: The cranial implant of any one of examples 22 to 33, wherein the cranial implant defines a pair of edges extending a length of the cranial implant such that the pair of edges define a longitudinal slot along the length of the cranial implant and through the interior guide portion and the exterior guide portion.

Example 35: The cranial implant of any one of examples 22 to 34, further comprising an adhesive disposed on the outer surface of the interior guide portion.

Example 36: The cranial implant of any one of examples 22 to 35, wherein the elongated member comprises a medical lead comprising one or more electrodes.

Example 37: A system comprising: a cranial implant comprising: an interior guide portion configured to be disposed in a burr hole of a cranium, the interior guide portion comprising a first distal end, a first proximal end, a first inner surface, and a first outer surface, the distal end configured to be inserted further into the burr hole than the proximal end, and the first inner surface at least partially defines a channel configured to accept an elongated member; and an exterior guide portion extending from the interior guide portion and configured to contact an external surface of the cranium, the exterior guide portion comprising a second distal end, a second proximal end, a second inner surface, and a second outer surface, wherein the second inner surface at least partially defines the channel extending from the interior guide portion, and wherein a second diameter of the outer surface of the exterior guide portion is larger than a first diameter of the first outer surface of the interior guide portion; and a plug retainer configured to contact the exterior guide portion.

Example 38: The system of example 37, wherein the plug retainer is configured to hold the cranial implant while removing a cannula, wherein the plug retainer comprises at least one surface feature on an outer surface of the plug retainer configured to provide friction against a hand of a user.

Example 39: The system of example 38, wherein the at least one surface feature of the plug retainer comprises at least one of a wing, fin, rib, bump, or textured surface.

Example 40: The system of any one of examples 37 to 39, wherein the channel is a first channel, and further comprising a fixation cap configured to contact the cranium, the fixation cap defining a recess that accepts the exterior guide portion, defining a second channel configured to accept a portion of the elongated member extending out from the first channel, and defining a curved track, wherein the curved track is configured to facilitate the elongated member being wrapped within the curved track and around the fixation cap.

Example 41: The system of example 40, further comprising a bone screw configured to secure the fixation cap to the cranium.

Example 42: The system of any one of examples 37 to 41, further comprising a fixation plate configured to contact the cranium and secure the elongated member on the external surface of the cranium.

Example 43: A method comprising: inserting a cranial implant into a burr hole configured to retain an elongated member with respect to the cranium, the cranial implant comprising: an interior guide portion configured to be disposed in a burr hole of a cranium, the interior guide portion comprising a distal end, a proximal end, an inner surface, and an outer surface, the distal end configured to be inserted further into the burr hole than the proximal end, and the inner surface configured to at least partially define a channel that accepts an elongated member; and an exterior guide portion extending from the interior guide portion and configured to contact an external surface of the cranium, the exterior guide portion comprising a distal end, a proximal end, an inner surface, and an outer surface, and the inner surface configured to at least partially define the channel extending from the interior guide portion, wherein a diameter of the outer surface of the exterior guide portion is larger than a diameter of the outer surface of the interior guide portion; and inserting the elongated member from an exterior of a cranium through a burr hole and to a target site within the cranium.

Example 44: The method of example 43, further comprising loading the cranial implant onto a cannula and delivering the cranial implant into the burr hole.

Example 45: The method of example 44, further comprising loading a plug retainer onto the cannula to insert the cranial implant into the burr hole and retain the cranial implant within the burr hole while removing the cannula from the burr hole.

Example 46: The method of any one of examples 43 to 45, further comprising: winding an excess length of the elongated member around a track disposed on an underside of a fixation cap; placing the fixation cap over the cranial implant; and securing the fixation cap to the cranium.

It should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Various examples have been described. These and other examples are within the scope of the following claims.

What is claimed is:

1. A cranial implant comprising:
an arcuate interior guide portion configured to be disposed in a burr hole of a cranium, the arcuate interior guide portion comprising a distal end, a proximal end, an inner surface, and an outer surface, the distal end configured to be inserted further into the burr hole than the proximal end, and the inner surface at least partially defines a first channel configured to accept an elongated member, wherein the outer surface is configured to extend from a first end to a second end around less than a full circumference of the burr hole thereby defining a circumferential gap between the first end and the second end, and wherein for the inner surface and the outer surface to meet at each of the first end and the second end, a distance between the inner surface and the outer surface gradually decreases; and
an exterior guide portion defining an exterior facing surface and an inward facing surface, the exterior guide portion extending from the arcuate interior guide portion and configured to contact an external surface of the cranium with the inward facing surface, the exterior guide portion comprising: a first inner edge segment defining a first wall that defines a first side of a second channel, and a second inner edge segment defining a second wall that defines a second side of the second channel, wherein the second channel is configured to accept the elongated member between the first wall and the second wall, wherein the exterior guide portion comprises one or more flange structures extending from at least one of a portion of the first wall toward the second wall or a portion of the second wall toward the first wall to define at least a top side of the second channel and at least partially enclose the second channel, and wherein each of the one or more flange structures define a top surface continuous with the exterior facing surface and a bottom surface; and wherein the bottom surface of the one or more flange structures are configured to retain the elongated member between the first wall and the second wall at least partially within the second channel.

2. The cranial implant of claim 1, wherein an inner diameter of the arcuate interior guide portion is greater than an outer diameter of a cannula, an outer diameter of the arcuate interior guide portion is configured to be greater than a diameter of the burr hole in order to provide cranial implant retention in the burr hole, the gradually decreasing distance between the inner surface and the outer surface is configured to make the arcuate interior guide portion progressively more radially flexible, and an inner diameter of the distal end of the arcuate interior guide portion is less than an outer diameter of the elongated member inserted in the cranial implant in order to retain the elongated member in the cranial implant.

3. The cranial implant of claim 1, wherein the cranial implant is constructed of at least one of silicone, polyurethane, or low-density polyethylene (LDPE).

4. The cranial implant of claim 1, wherein an outer diameter of the arcuate interior guide portion extends from about 3 millimeters (mm) to about 8 mm such that the outer diameter is configured for the burr hole that has a diameter range that extends from about 2 millimeters (mm) to about 7 mm.

5. The cranial implant of claim 1, wherein an outer diameter of the arcuate interior guide portion extends from about 3 millimeters (mm) to about 8 mm and the cranial implant is configured to be inserted in the burr hole.

6. The cranial implant of claim 1, wherein the cranial implant defines a pair of edges extending a length of the cranial implant as the first end and the second end such that the pair of edges define a longitudinal slot along the length of the cranial implant and through the arcuate interior guide portion such that the outer surface is configured to extend around less than the full circumference of the burr hole.

7. The cranial implant of claim 1, further comprising an adhesive disposed on the outer surface of the arcuate interior guide portion.

8. The cranial implant of claim 1, wherein the elongated member comprises a medical lead comprising one or more electrodes.

9. The cranial implant of claim 1, wherein the first channel defines a center axis, and wherein the exterior guide portion extends radially outward from the center axis, the exterior guide portion configured to extend over less than the full circumference of the burr hole.

10. The cranial implant of claim 1, wherein a center axis of the first channel is substantially orthogonal to a center axis of the second channel.

11. The cranial implant of claim 1, wherein the exterior guide portion comprises two wing segments coupled to the arcuate interior guide portion, and wherein each wing segment defines the respective first wall and the second wall to at least partially define the second channel.

12. The cranial implant of claim 1, further comprising a fixation cap configured to contact the cranium, the fixation cap defining a recess that accepts the exterior guide portion, defining a third channel configured to accept a portion of the elongated member extending out from the second channel, and defining a curved track, wherein the curved track is configured to facilitate the elongated member being wrapped within the curved track and around the fixation cap.

13. A system comprising:
a cranial implant comprising:
an arcuate interior guide portion configured to be disposed in a burr hole of a cranium, the arcuate interior guide portion comprising a distal end, a proximal end, an inner surface, and an outer surface, the distal end configured to be inserted further into the burr hole than the proximal end, and the inner surface at least partially defines a first channel configured to accept an elongated member, wherein the outer surface is configured to extend from a first end to a second end around less than a full circumference of the burr hole thereby defining a circumferential gap between the first end and the second end, and wherein for the inner surface and the outer surface to meet at each of the first end and the second end, a distance between the inner surface and the outer surface gradually decreases; and
an exterior guide portion defining an exterior facing surface and an inward facing surface, the exterior guide portion extending from the arcuate interior guide portion and configured to contact an external surface of the cranium with the inward facing surface, the exterior guide portion defining a second channel configured to accept the elongated member, wherein the exterior guide portion comprises one or more flanges coupled to the exterior guide portion and wherein each of the one or more flange structures define a top surface continuous with the exterior facing surface and a bottom surface; and the bottom surface of the one or more flange structures are configured to retain the elongated member at least partially within the second channel; and
a fixation device comprising:
a recess that accepts the exterior guide portion; and
a third channel on an underside of the fixation device configured to accept a portion of the elongated member extending out from the second channel,
wherein the fixation device is configured to contact the external surface of the cranium.

14. The system of claim 13, wherein the fixation device comprises a fixation cap, wherein the third channel of the fixation cap defines a curved track, wherein the curved track is configured to facilitate the elongated member being wrapped within the curved track and around the fixation cap.

15. The system of claim 13, further comprising a bone screw configured to secure the fixation device to the cranium.

16. The system of claim 13, wherein the fixation device comprises a fixation plate configured to contact the cranium and secure the elongated member on the external surface of the cranium.

17. A method comprising:
inserting a cranial implant into a burr hole configured to retain an elongated member with respect to a cranium, the cranial implant comprising:
an arcuate interior guide portion configured to be disposed in the burr hole of the cranium, the arcuate interior guide portion comprising a distal end, a proximal end, an inner surface, and an outer surface, the distal end configured to be inserted further into the burr hole than the proximal end, and the inner surface configured to at least partially define a first channel that accepts the elongated member, wherein the outer surface is configured to extend from a first end to a second end around less than a full circumference of the burr hole thereby defining a circumferential gap between the first end and the second end, and wherein for the inner surface and the outer surface to meet at each of the first end and the second end, a distance between the inner surface and the outer surface gradually decreases; and an exterior guide portion defining an exterior facing surface and an inward facing surface, the exterior guide portion extending from the arcuate interior guide portion and configured to contact an external surface of the cranium with the inward facing surface, the exterior guide portion comprising a first inner edge segment defining a first wall that defines a first side of a second channel, and a second inner edge segment defining a second wall that defines a second side of the second channel, wherein the second channel is configured to accept the elongated member between the first wall and the second wall, wherein the exterior guide portion comprises one or more flange structures extending from at least one of a portion of the first wall toward the second wall or a portion of the second wall toward the first wall to define at least a top side of the second channel and at least to partially enclose the second channel, and wherein each of the one or more flange structures define a top surface continuous with the exterior facing surface and a bottom surface; and wherein the bottom surface of the one or more flange structures are configured to retain the elongated member between the first wall and the second wall at least partially within the second channel; and inserting the elongated member from an exterior of the cranium through the burr hole and to a target site within the cranium.

18. The method of claim 17, further comprising:

winding an excess length of the elongated member around a track disposed on an underside of a fixation cap;

placing the fixation cap over the cranial implant; and securing the fixation cap to the cranium.

19. The method of claim 17, further comprising securing the elongated member to the cranium by attaching a fixation cap over a portion of the elongated member extending through the second channel and away from the burr hole.

20. The method of claim 17, wherein inserting the cranial implant comprises inserting the cranial implant into the burr hole after inserting the elongated member through the burr hole.

21. The method of claim 17, further comprising pressing the elongated member between the one or more flange structures to secure the elongated member within the second channel.

* * * * *